(12) United States Patent
Bergman

(10) Patent No.: US 8,534,282 B2
(45) Date of Patent: Sep. 17, 2013

(54) FLEXIBLE SELF-INFLATING RESUSCITATOR SQUEEZE BAG AUTOMATION DEVICE, SYSTEM, AND METHOD

(75) Inventor: Robert Todd Bergman, Columbus, IN (US)

(73) Assignee: Columbus Oral and Maxillofacial Surgery P.S.C., Columbus, IN (US)

(*) Notice: Subject to any disclaimer, the term of this patent is extended or adjusted under 35 U.S.C. 154(b) by 32 days.

(21) Appl. No.: 13/401,101

(22) Filed: Feb. 21, 2012

(65) Prior Publication Data
US 2012/0145151 A1   Jun. 14, 2012

Related U.S. Application Data

(63) Continuation of application No. PCT/US2010/038812, filed on Jun. 16, 2010, which is a continuation-in-part of application No. 12/545,467, filed on Aug. 21, 2009.

(51) Int. Cl.
*A61M 16/00* (2006.01)

(52) U.S. Cl.
USPC ............ 128/205.16; 128/203.28; 128/204.28; 128/205.13

(58) Field of Classification Search
USPC   128/203.28, 204.18, 204.28, 205.13–205.17; 600/540–541
See application file for complete search history.

(56) References Cited

U.S. PATENT DOCUMENTS

| | | | |
|---|---|---|---|
| 2,225,201 A * | 12/1940 | Anderson | 128/204.21 |
| 2,761,445 A | 9/1956 | Cherkin | |
| 2,924,215 A | 2/1960 | Goodner | |
| 3,283,754 A * | 11/1966 | Goodner | 128/205.14 |
| 3,364,924 A * | 1/1968 | Barkalow | 601/106 |
| 3,757,776 A | 9/1973 | Bauman | |
| 3,818,806 A * | 6/1974 | Fumagalli | 92/13.2 |
| 4,384,576 A * | 5/1983 | Farmer | 128/205.18 |
| 4,409,977 A | 10/1983 | Bisera et al. | |
| 4,452,241 A | 6/1984 | Sarnoff et al. | |
| 4,621,984 A | 11/1986 | Fussell | |
| 4,898,166 A | 2/1990 | Rose et al. | |
| 5,222,491 A * | 6/1993 | Thomas | 128/205.13 |
| 5,342,313 A | 8/1994 | Campbell et al. | |
| 5,345,929 A * | 9/1994 | Jansson et al. | 128/205.13 |
| 5,427,091 A | 6/1995 | Phillips | |
| 5,478,211 A | 12/1995 | Dominiak et al. | |
| 5,551,416 A * | 9/1996 | Stimpson et al. | 128/200.16 |

(Continued)

OTHER PUBLICATIONS

Chandler, David L., "In the World: Breath of Life", http://web.mit.edu/newsoffice/2010/itw-ventilator-0715.html, Jul. 15, 2010.

(Continued)

*Primary Examiner* — Justine Yu
*Assistant Examiner* — Christopher Miller
(74) *Attorney, Agent, or Firm* — Roberts IP Law; John Roberts

(57) ABSTRACT

A device for automatically squeezing and releasing an AMBU-bag is disclosed. A device has a housing and a mechanical compression squeezer in the housing. There are openings in the housing for inlet tubes and outlet tubes of AMBU-bag to pass in and out of the housing. A powered actuator powers the compression squeezer. Alarms and signals provide information regarding excessive pressure and regarding bag cycling.

32 Claims, 28 Drawing Sheets

(56) References Cited

U.S. PATENT DOCUMENTS

| | | | |
|---|---|---|---|
| 5,628,305 A | 5/1997 | Melker | |
| 5,664,563 A | 9/1997 | Schroeder et al. | |
| 5,711,295 A | 1/1998 | Harris | |
| 5,769,072 A | 6/1998 | Olsson et al. | |
| 6,263,873 B1 | 7/2001 | Hedenberg | |
| 6,328,036 B1 | 12/2001 | Emtell et al. | |
| 6,397,844 B1 | 6/2002 | Wennerholm et al. | |
| 7,284,554 B2 * | 10/2007 | Shaw | 128/205.13 |
| 7,334,578 B2 | 2/2008 | Biondi et al. | |
| 2004/0025873 A1 | 2/2004 | Padgett | |
| 2004/0230140 A1 | 11/2004 | Steen | |
| 2005/0085799 A1 | 4/2005 | Luria | |
| 2005/0284472 A1 * | 12/2005 | Lin | 128/202.29 |
| 2006/0260612 A1 | 11/2006 | Matthiessen et al. | |
| 2007/0028921 A1 | 2/2007 | Banner et al. | |
| 2007/0045152 A1 * | 3/2007 | Kwok et al. | 206/733 |
| 2007/0068518 A1 * | 3/2007 | Urias et al. | 128/200.24 |
| 2007/0169780 A1 | 7/2007 | Halpern et al. | |
| 2008/0251082 A1 * | 10/2008 | Sinha | 128/207.16 |
| 2008/0257351 A1 | 10/2008 | Gitschlag | |
| 2009/0069726 A1 | 3/2009 | Sherman et al. | |
| 2009/0126734 A1 * | 5/2009 | Dunsmore et al. | 128/203.25 |
| 2010/0132708 A1 * | 6/2010 | Martin et al. | 128/204.17 |

OTHER PUBLICATIONS

CIMIT Blog: Low-Cost Ventilator: Life Changing/Life Saving Inventions at MIT, http://www.cimitblog.org/cimit_forum_blog/2010/02, Feb. 18, 2010.

* cited by examiner

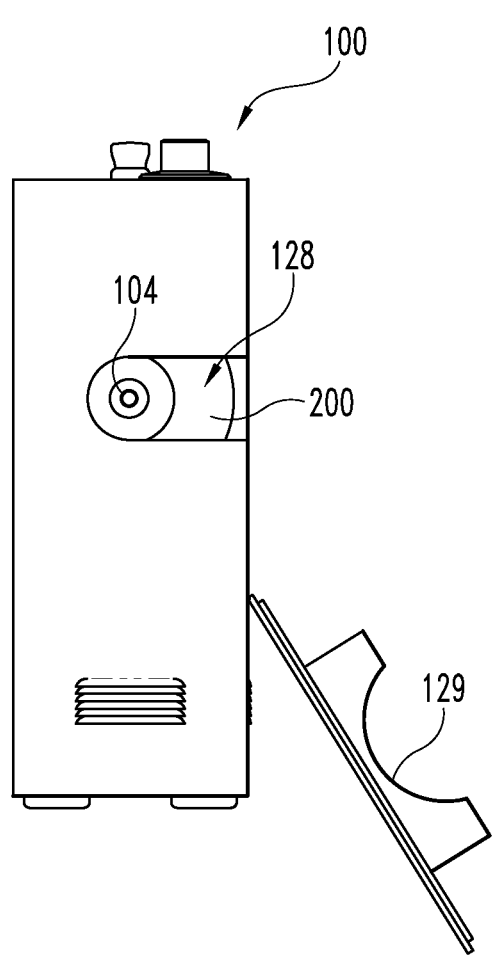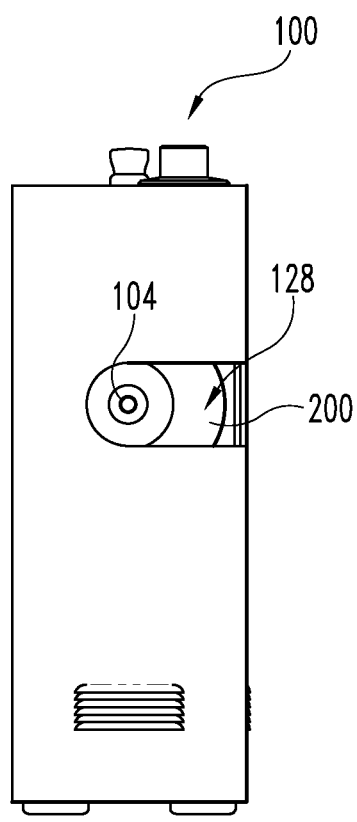
*Fig. 2C*            *Fig. 2D*

US 8,534,282 B2

FLEXIBLE SELF-INFLATING RESUSCITATOR SQUEEZE BAG AUTOMATION DEVICE, SYSTEM, AND METHOD

CROSS-REFERENCE TO RELATED APPLICATION

This application is a continuation of International Application No. PCT/US2010/038812, filed Jun. 16, 2010, which is, a continuation-in-part of application Ser. No. 12/545,467, filed Aug. 21, 2009, which are hereby incorporated by reference. I hereby claim priority to each of the foregoing applications.

FIELD OF INVENTION

The present invention relates to flexible self-inflating resuscitator squeeze bags, and more specifically, devices, systems, and methods for automatically squeezing and/or releasing flexible self-inflating resuscitator squeeze bags.

BACKGROUND

Flexible self-inflating resuscitator squeeze bags are in widespread use in medical and emergency treatment of patients. They are designed to be manually squeezed, such as by a doctor, nurse, orderly, EMT or other medical service provider. Their usage includes, for example, respirating a patient (civilian or soldier) in the field and/or during transport to a hospital. Their usage also includes maintaining patient respiration during movement from one location to another. For example, a flexible self-inflating resuscitator squeeze bag may be used on a patient being transported on a gurney from their hospital room (where they are ordinarily hooked-up to a respirator) to a surgical operating room, where they are then hooked-up to a second respirator in the operating room. The flexible self-inflating resuscitator squeeze bag is typically manually operated during such movement of a patient. Otherwise, patients needing respiration are typically hooked-up to a respirator. The present device may be used to supplement limited inventories of respirators, as in the case of an epidemic or other high demand.

SUMMARY

The claims, and only the claims, define the invention. The present invention includes several, but not necessarily all, of a device for use with a flexible self-inflating resuscitator squeeze bag, the flexible self-inflating resuscitator squeeze bag having an intake tube at a first end and an outlet tube at an opposite end thereof. The device may have a housing for receiving the squeeze bag. The device may have an opening for the squeeze bag narrow intake tube, and another one optionally for the squeeze bag outlet tube.

A mechanical compression squeezer may be provided in the housing for cyclically squeezing a squeeze bag from its outside and releasing the squeeze for expansion. A power actuator, which may be controlled by an electronic timer, may be provided for powering the mechanical compression squeezer for cyclical squeezing.

Other optional features that may be included, but are not required, are set forth in the various dependent and independent claims.

BRIEF DESCRIPTION OF THE DRAWINGS

FIG. 2C is a side view, partially cut away, of the device of FIG. 1C.

FIG. 2D is a side view, partially cut away, of the device of FIG. 1D.

BRIEF DESCRIPTION OF THE PREFERRED EMBODIMENTS

Figure 1A:
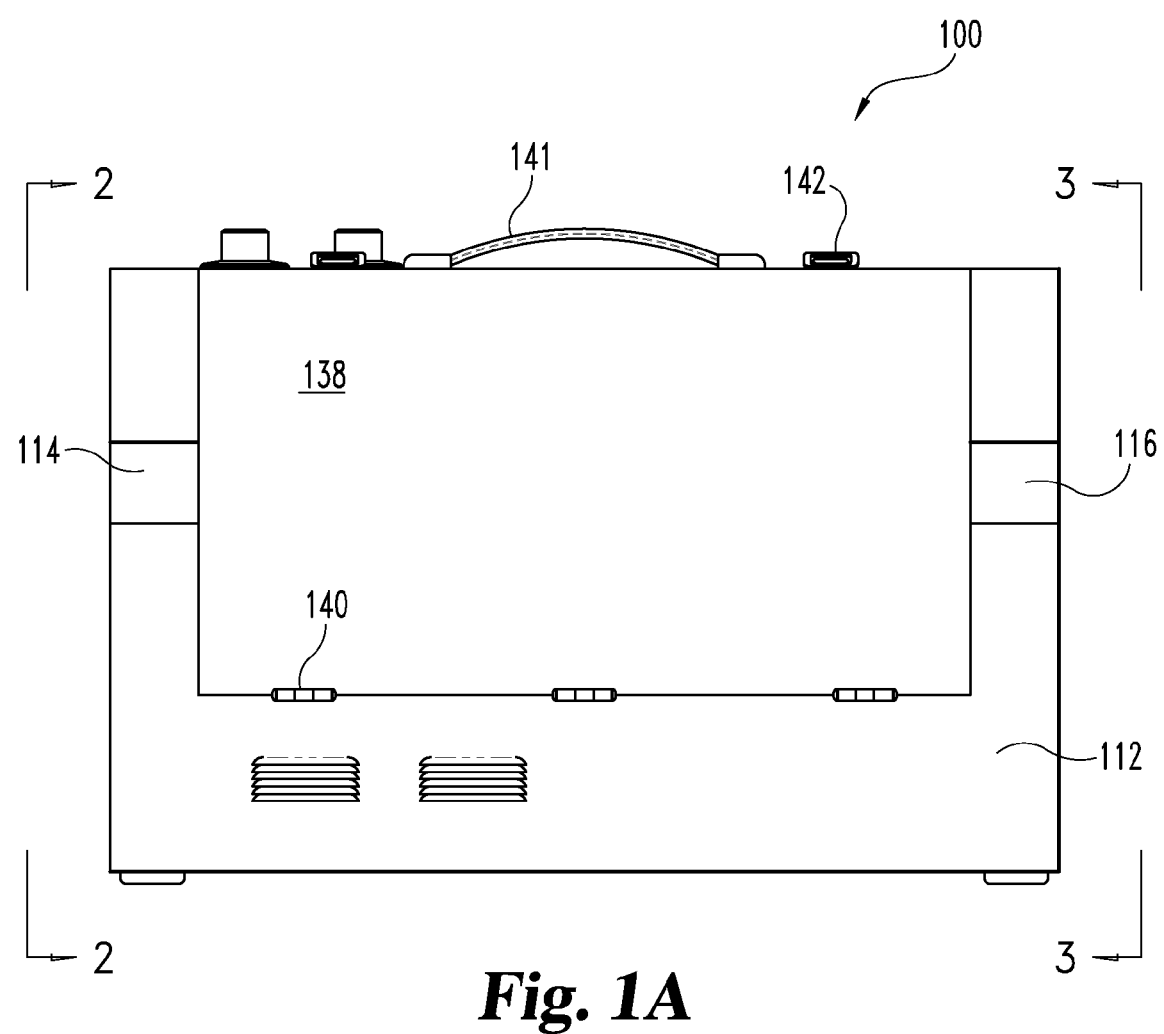
FIG. 1A is a front view of the device according to one example of the present invention with an optional lid closed, and with no flexible self-inflating resuscitator squeeze bag in it.

For the purposes of promoting an understanding of the principles of the invention, reference will now be made to the examples, sometimes referred to as embodiments, illustrated and/or described herein. These are mere examples. It will nevertheless be understood that no limitation of the scope of the invention is thereby intended. Such alterations and further modifications in the described processes, systems or devices, and any further applications of the principles of the invention as described herein, are contemplated as would normally occur to one skilled in the art to which the invention relates, now and/or in the future in light of this document.

As used in the claims and the specification, the following terms have the following defined meanings:

The term "flexible self-inflating resuscitator squeeze bag" means an ambulatory or movable bag that is manually squeezable to provide or assist in respiration of a patient, and is sometimes referred to generically as an "air-mask-bag-unit" or "AMBU-bag" that may or may not be associated with the Danish company Ambu A/S.

The term "base" means a structure at or comprising the bottom of a housing upon which it sits. A base may be optionally part of or not part of the housing.

The term "blood pressure meter" means any meter, electronic, hydraulic, mercury-based, or otherwise, that measures blood pressure of a patient.

The term "clean" means substantially free of germs and/or pathogens sufficient for medical and/or surgical exposure to a patient's lungs of gas passing through.

The term "$CO_2$ meter" means any meter that measures the amount of carbon dioxide exhaled by a patient.

The term "compression squeezer" means a mechanical, electro-mechanical, pneumatic, and/or hydraulic (unless denoted "non-pneumatic/hydraulic") component that provides force and/or pressure on an outside of a flexible self-inflating resuscitator squeeze bag to squeeze it to cause air/gas to flow through it.

The term "confine" means substantially restrict or hold in place.

The term "controlled" means controlled by an operator and/or computer processor to achieve a result or output.

The term "crank member" means a member that translates generally reciprocating motion from a rotating or revolving member. It may be a member that is straight, curved, bent, not bent, flat or any other shape.

The term "cycle frequency" means the frequency, typically measured in breaths per minute, of squeezing and releasing a flexible self-inflating resuscitator squeeze bag.

The term "cyclically" means a repetitious cycle, typically although not always of a consistent frequency.

The term "detachment of said intake tube" means operator separation of intake tube, directly or indirectly, from the remaining portion of the flexible self-inflating resuscitator squeeze bag.

The term "detachment of said outlet tube" means operator separation of outlet tube, directly or indirectly, from the remaining portion of the flexible self-inflating resuscitator squeeze bag.

The term "distal attachments" means various tubes, hoses, patient mouth pieces, masks, and/or patient tracheotomy attachments, attached with the outlet of a flexible self-inflating resuscitator squeeze bag.

The term "drop-in insertion" means the inserting of a flexible self-inflating resuscitator squeeze bag into place without requiring substantial mechanical disassembly and/or assembly.

The term "electronic blood-oxygen level sensor" means a sensor of a patient's blood oxygen level that takes an output and transforms it into an electronic signal which is then translated into a numeric and/or alpha-numeric indicator of blood oxygen level. This can include, but is not limited to, sensors utilizing light or other transmissive frequency through a finger or other body part to provide input data to determine blood oxygen level.

The term "electronic timer" means a timer, typically in seconds, which is electrical rather than mechanical.

The term "end" means one or either ends of an elongated structure, such as for example an elongated flexible self-inflating resuscitator squeeze bag or an elongated housing, as opposed to its sides.

The term "expansion" means to increase volume.

The term "end member" means a structure at or near one end of the flexible self-inflating resuscitator squeeze bag. It may be rigid, flexible, or both.

The term "fixed portion" means substantially rigid or substantially immovable with respect to the housing when in use.

The term "flexible" means bendable or pliable to allow expansion and squeezing.

The term "flexible tension member" means one or more flexible belts, straps, cables, cords or the like.

The term "holding" means maintaining and/or capable of substantially maintaining something in position with respect to something else.

The term "hooks" means a mechanical structure strong enough to hang the housing from.

The term "hoop stress" means circumferential loading around all, or more typically a portion, of the bag for causing squeezing of the bag.

The term "housing" means an outer case, shell, frame, grid, or structure. It may be partially or wholly solid material, mesh or cage structure, and/or both. It may be made from a variety of materials, although metal and/or rigid plastic are preferred. It may be opaque, transparent, translucent, and/or a combination of the above.

The term "intake tube" means a tube or conduit (regardless of cross section, round, square, rectangle, oblong or otherwise) which may be rigid, flexible, and/or both, which is attached to or near the intake of the bag.

The term "magnitude of squeezing" means the amount of squeezing into the flexible self-inflating resuscitator squeeze bag, corresponding (directly and/or non-linearly) to the amount of air/gas flowing through the bag.

The term "mechanical" means other than by human muscle and/or bone and/or exhalation force.

The term "movable rigid member" means one or more rigid members that are designed to move, either by translation, pivoting or otherwise, with respect to the housing. The rigidity may be variable, but preferably substantially rigid.

The term "movement pausing" means slowing and/or stopping of movement. This may include linear slowing, sudden slowing, or any other rate or profile of deceleration.

The term "near" means close enough to functionally achieve inter-operability between two parts, directly, indirectly and/or with or without one or more intervening parts.

The term "open-close lid" means a lid which has at least two positions, one position being open and the other position being closed.

The term "opening" means one or more holes, slots, apertures, and/or slots in a member, wall, mesh, cage, or the like.

The term "operator adjustment" means capable of being adjusted or modified by the operator.

The term "opposite" means opposed to or generally across from.

The term "outlet tube" means a tube or conduit (regardless of cross section, round, square, rectangle, oblong or otherwise) which may be rigid, flexible, and/or both, which is attached to the outlet of the bag.

The term "outside" means not from within. For example, the outside of a flexible self-inflating resuscitator squeeze bag means the outer portion which is squeezed, as opposed to the inner surface of a bag.

The term "portable" means sufficiently light and small that it can be carried by a single adult human.

The term "powered actuator" means a mechanism that provides movement other than by human power. This includes, but is not limited to electrical power, mechanical power, hydraulic power, pneumatic power, and/or a combination thereof. Frequently, but not necessarily a powered actuator includes one or more electrical motors.

The term "receiving" means taking or being capable of taking one thing within (partially or wholly) or in engagement or connection with another.

The term "recessable" means partially and/or wholly receiving one component within a recess. Preferably, once something is recessable, it is fully flushed or below fully flushed with respect to a reference surface, although optionally can include being partially recessed.

The term "releasing" means the opposite of squeezing.

The term "running" means from one location to another location.

The term "shaped to correspond to at least a portion of the generally cylindrically curved outer surface" means, for a region, a surface or surfaces and/or edges that collectively form a generally cylindrical shape. These may be, but do not have to be curved, and may include several flat surfaces, edges and points arrayed in a general cylinder, or more often a part or frustum of a cylinder.

The term "slot" means an opening that is generally longer than it is wide. A slot may be linear, curved, serpentine or otherwise, and correspondingly the length of the slot would be linear, curved and/or serpentine.

The term "squeeze bag" means a portion of a flexible self-inflating resuscitator squeeze bag that may be squeezed and released to cause air/gas flow.

The term "volume controller" means a knob, slide, key pad, or other user input and associated electrical components to increase, decrease and/or maintain the amount air/gas squeezed through the squeeze bag.

The term "volume of air/gas per cycle" means the amount of air/gas, typically expressed in cubic inches per minute, cubic inches per second, cubic liters and/or centiliters per minute and/or per second for a given squeeze and release for a squeeze bag.

The term "yoke" means a mechanical structure, typically alone or in combination with other parts confining on three or four sides of another member or tube. Optionally, the yoke may be capped or uncapped, such that the fourth, optionally open side of the yoke may be closed or capped. The yoke may be rigid or flexible, but preferably it is rigid or substantially rigid. The yoke may be lined or unlined with softer material, or friction increasing material (such as rubber or otherwise). The yoke may be of a variety of shapes, including rounded, rectilinear, or otherwise. A yoke may be defined, in whole or in part, by the edge of a slot or other opening.

Articles and phrases such as "the", "a", "an", "at least one", and "a first" are not limited to mean only one, but rather are inclusive and open ended to also include, optionally, multiple such elements. Likewise, "comprising" is open ended and inclusive.

Referring to the drawing figures, these are only examples of the invention, and the invention is not limited to what is shown in the drawings.

As but an example of a device, device 100 is for use with the flexible self-inflating resuscitator squeeze bag assembly 102 having a flexible squeeze bag 200. Another example is device 300 shown in FIGS. 11A-17. That device 300 has analogous components which are typically denoted with a "300" series reference number generally corresponding to a "100" series reference number of device 100. Ordinarily, the flexible self-inflating resuscitator squeeze bag is initially clean, particularly on its inner surfaces that contact air/gas to the patient, and it may optionally be a one-time use or disposable product. Preferably, the squeeze bag has an intake tube 104 (shown with broken lines) at a first end 106 of the flexible self-inflating resuscitator squeeze bag, and an outlet tube 108 (shown with broken lines) at an opposite end 110 of the flexible self-inflating resuscitator squeeze bag. Device 100 preferably comprises a housing 112 for receiving squeeze bag 200 (see FIG. 1C). In one example, the housing is generally rectangular, preferably elongated, although it may be any shape (square, cylindrical, or otherwise).

Figure 4:
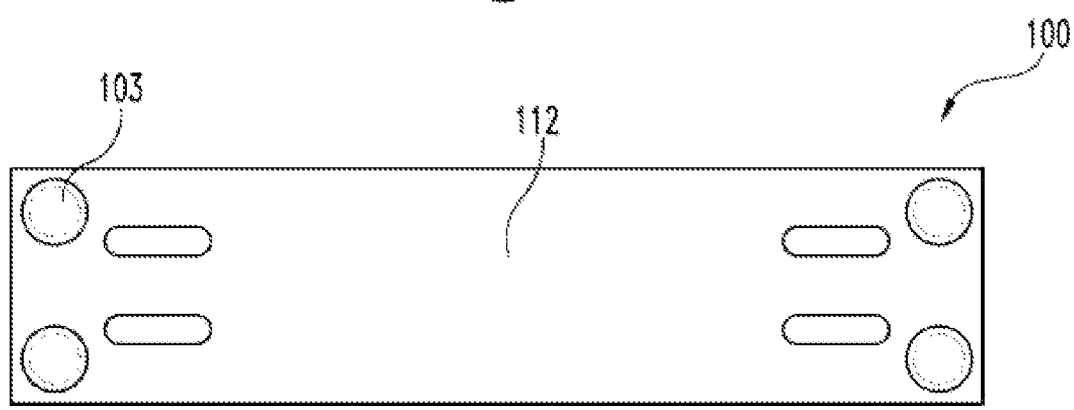
FIG. 4 is a bottom view of the device of FIG. 3.
Figure 16:
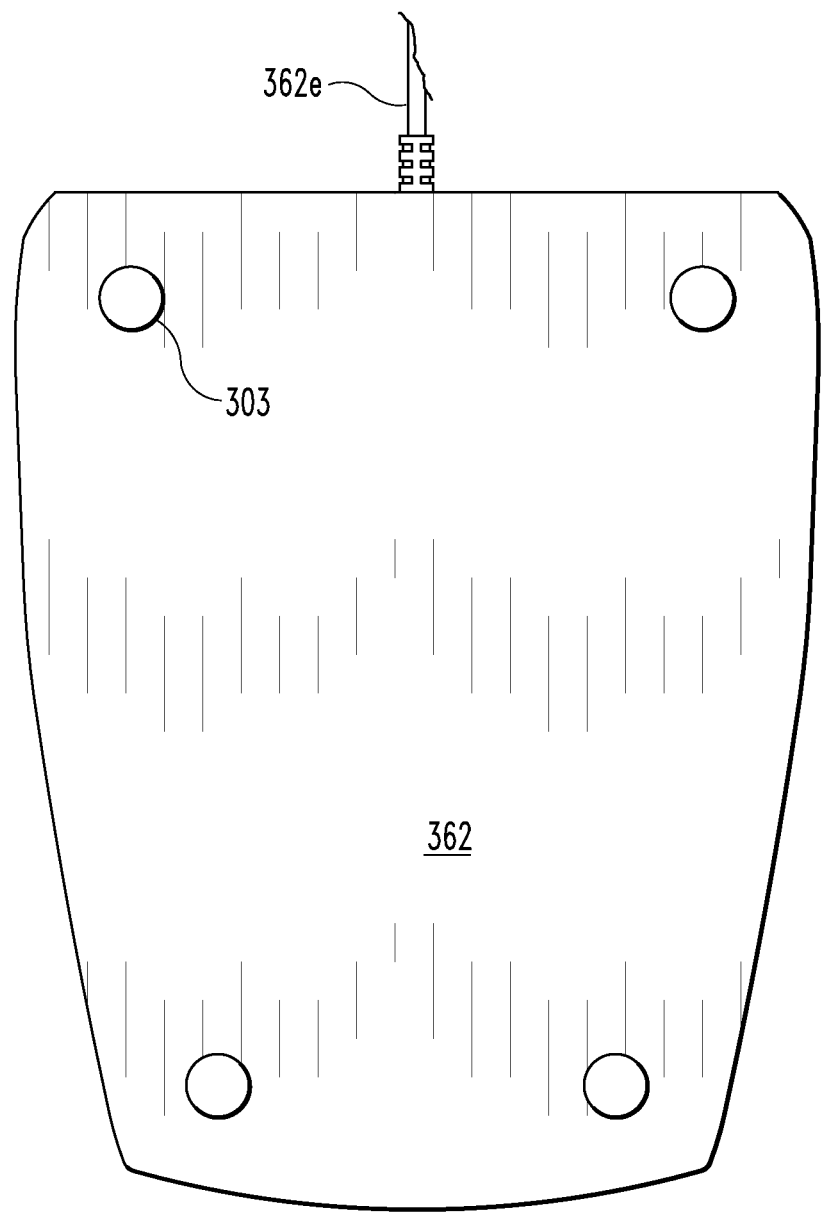
FIG. 16 is a bottom plan view of the device of FIG. 11A.

Optionally, the bottom of housing 112 may include several rubber feet, such as rubber feet 103, 303 (see FIGS. 4, 16). Feet may be located elsewhere, such as opposite opening 124. Also, as illustrated in the various figures, ventilation slots and/or louvers may optionally be provided to facilitate cooling of the electronics, battery and/or actuators.

Optionally, but preferably, first yoke 114 may be on the housing for holding the flexible self-inflating resuscitator squeeze bag near intake tube 104. Also, optionally, a second yoke 116 may be provided on the housing for holding the flexible self-inflating resuscitator squeeze bag near outlet tube 108.

Figure 1B:
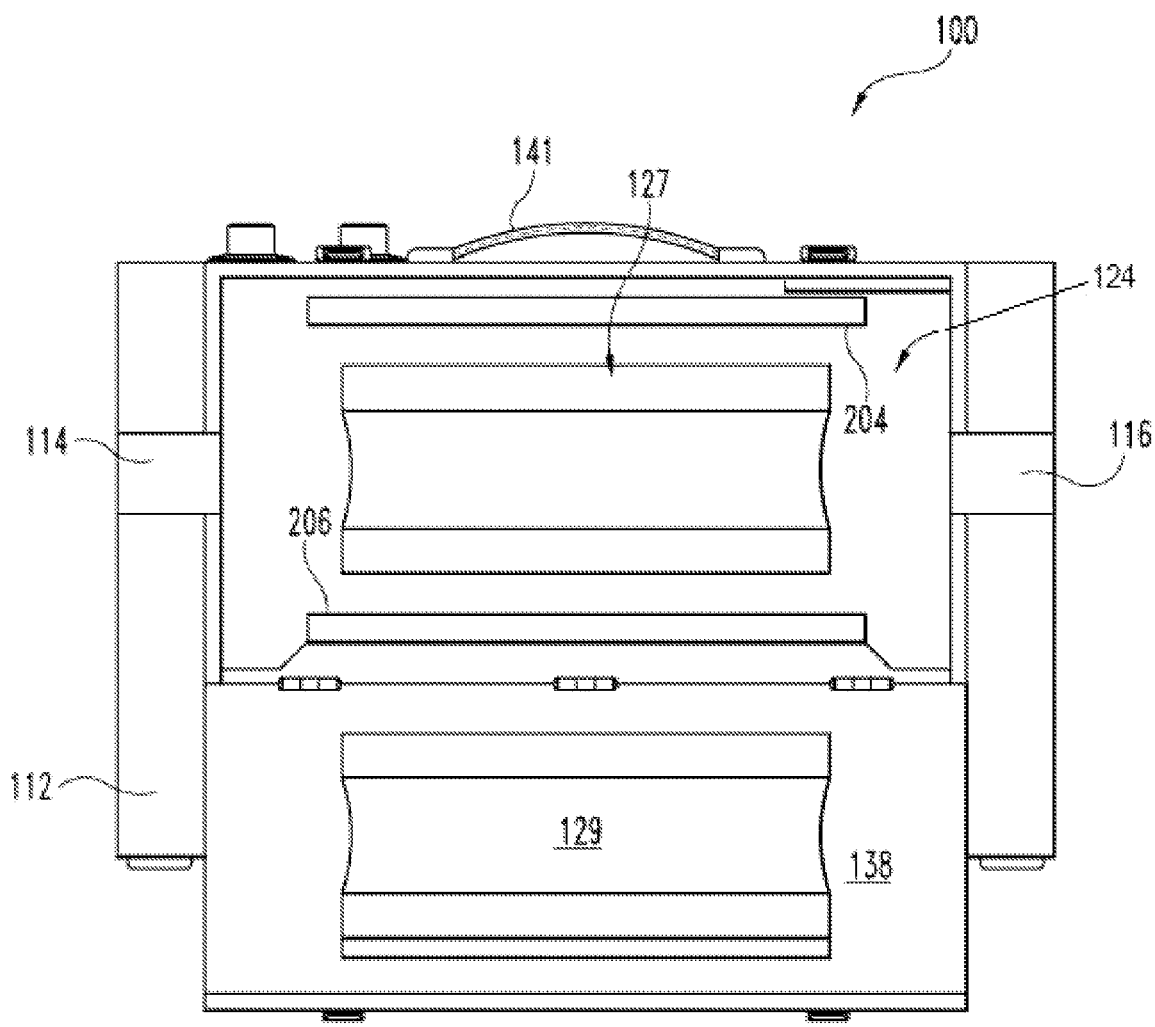
FIG. 1B shows the device in FIG. 1A with the lid open.
Figure 1C:
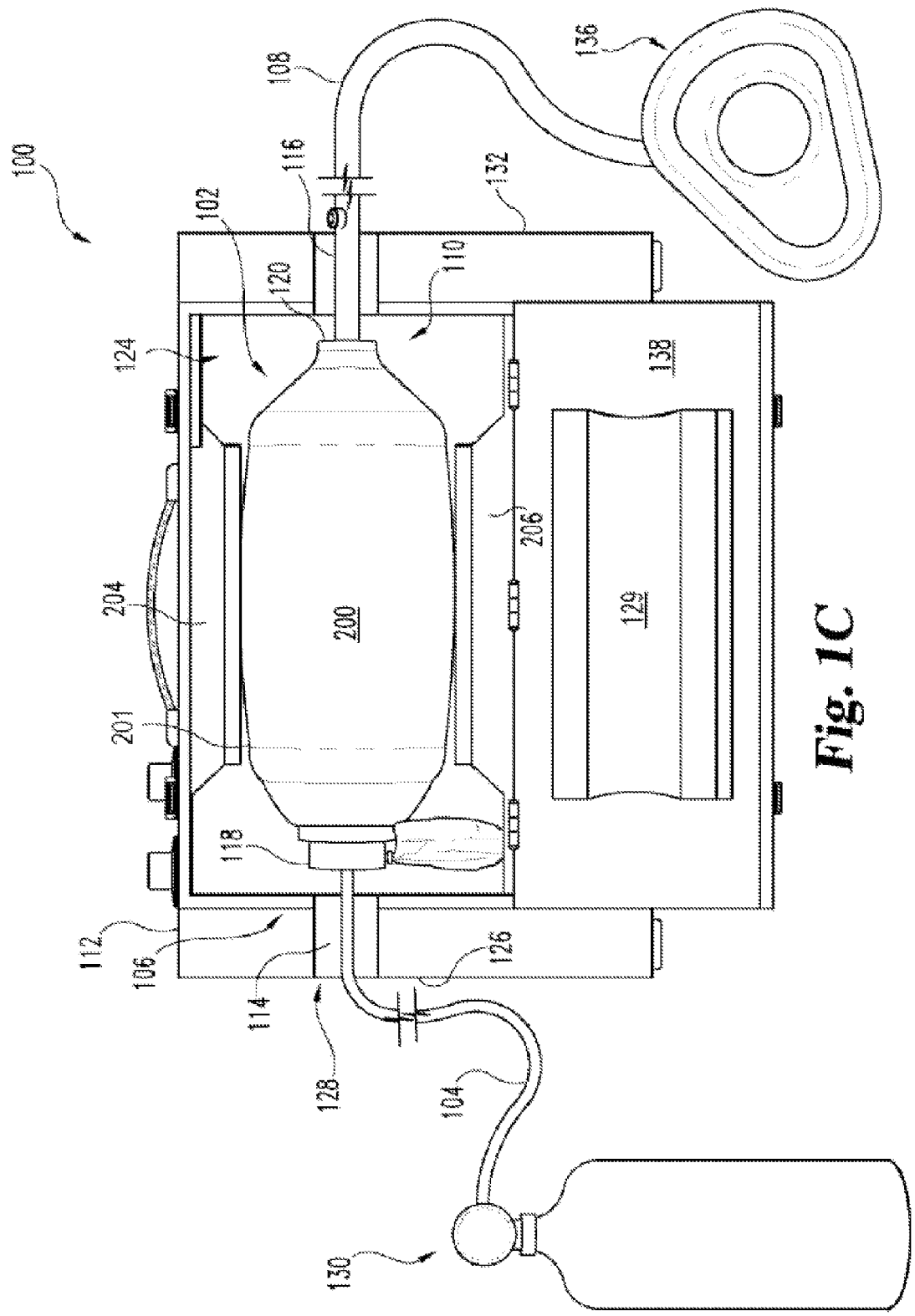
FIG. 1C shows the device of FIG. 1B with a flexible self-inflating resuscitator squeeze bag in the housing.
Figure 1D:
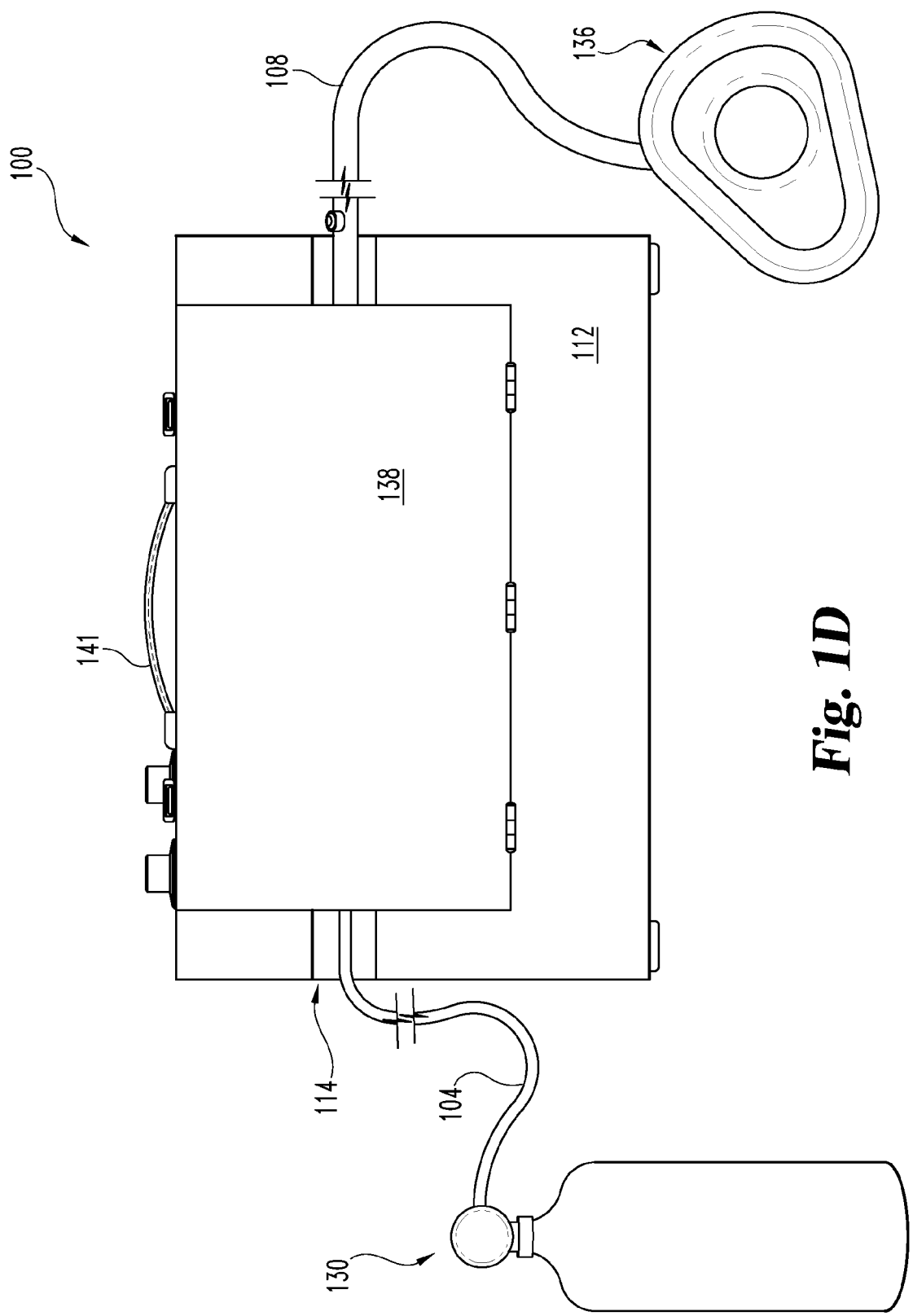
FIG. 1D shows the device of FIG. 1C with the lid closed.

Note that as illustrated in FIG. 1C, this one particular example shows yoke 114 and 116 holding inlet tube 104, and outlet tube 108 respectively. However, optionally, one or more of these yokes may be positioned and/or shaped closer to the flexible self-inflating resuscitator squeeze bag such that the yoke partially or completely holds collar 118 and/or collar 120. Further optionally, such yoke may hold the flexible self-inflating resuscitator squeeze bag partially axially inward of such collars and/or a combination of holding the inlet and/or outlet tubes, collars, and locations inboard thereof, alone or in combination. Moreover, the yoke does not necessarily have to coexist with an opening in the housing, but rather may be a separate structure. For example, the yoke may be a separate structure inside the housing, with an associated opening to allow ingress of tube 104 and egress of tube 108.

Preferably, one or more mechanical compression squeezers are part of device 100, preferably in housing 112. Mechanical compression squeezers, as defined herein, can be of a variety of configurations. As mere examples, various mechanical compression squeezers are illustrated in FIGS. 6A-6G, discussed further below. The mechanical compression squeezer (and/or squeezers) are for cyclically squeezing squeeze bag 200 from its outside 201 (see FIG. 1C) and releasing the squeeze bag for expansion. Note that FIG. 1C illustrates the squeeze bag in an expanded state.

Typically, a powered actuator is controlled by an electronic controller and/or timer 122 (see e.g., FIG. 9) for powering the mechanical compression squeezer for this cyclical squeezing.

Preferably, there is an opening 124 in the housing, wherein the opening allows drop-in insertion of the squeeze bag within the housing. For example, opening 124 is illustrated in FIG. 1B prior to insertion of the squeeze bag, whereas FIG. 1C shows opening 124 after the squeeze bag 200 has been dropped within the housing.

Optionally, a first end member 126 has a first slot or other opening 128 or opening 328 (see FIGS. 11A, 11B and 12), preferably running from the opening 124 in the housing to allow drop-in insertion of the flexible self-inflating resuscitator squeeze bag without requiring detachment of the intake tube 104 from distal attachments 130 to the intake tube 104. Optionally, but preferably, such drop-in insertion in slot 128 likewise allows drop-in insertion of the flexible self-inflating resuscitator squeeze bag in the housing without requiring detachment of the intake tube from the flexible self-inflating resuscitator squeeze bag.

Optionally, a second end member 132 has a second slot or other opening 134 or opening 334 (see FIGS. 11A, 11B and 12) running from the opening 124 in the housing to allow drop-in insertion of the outlet tube 108 without requiring detachment of the outlet tube from distal attachments 136. Again, optionally, slot 134 may allow drop-in insertion of the outlet tube 108 without requiring detachment of the outlet tube from the flexible self-inflating resuscitator squeeze bag 102.

Figure 1E:
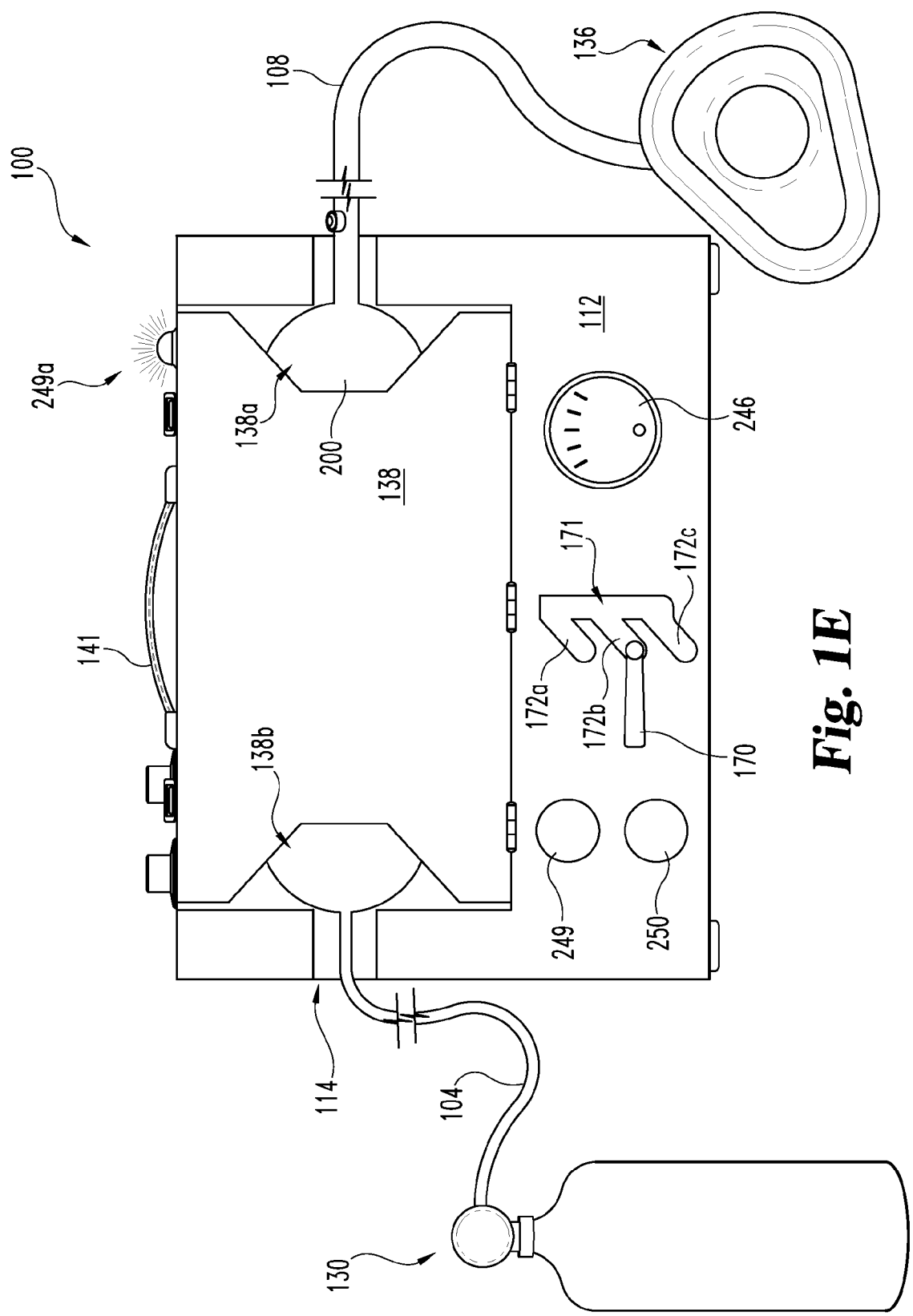
FIG. 1E shows an alternative device with the lid closed.

Optionally, an open-closed lid may be provided at opening 124 wherein the lid is openable to allow drop-in insertion of the squeeze bag within the housing and is closeable to confine the squeeze bag within the housing 112. When an open-close lid is used, it may be a solid material, mesh (see FIG. 11A, lid 329), bars, opaque, transparent, or otherwise. In the one example illustrated, it may include hinges such as hinge 140 and/or latches such as latch 142, although these are optional (see e.g., latch 342 in FIGS. 11A, 11B and 12). Furthermore, while opening 124 and/or lid 138 are, in this one illustrated example, shown on the front of the housing, they may be located elsewhere. Optionally, as shown in FIG. 1E, lid 138 may have recesses or openings 138a and/or 138b therein, making for improved visualization of bag 200. For example, they may be located on top, bottom, back or side of the housing as well as a combination thereof. For example, the opening may effectively wrap around two or more sides of the housing. Likewise, optionally the lid may wrap around such an opening.

Optionally, one or more confinement members, such as confinement members 127 and/or 129 and/or 327 and/or 329 may be included to help confine bag 200. In the examples shown, member 129 is on the lid 138 and when closed may confine a bag on member 127. They optionally may have partially curved surfaces, such as portions of a cylinder shaped surface as illustrated (see e.g., surface 327 in FIG. 11A), but also if used may have other shapes as well.

Figure 2A:
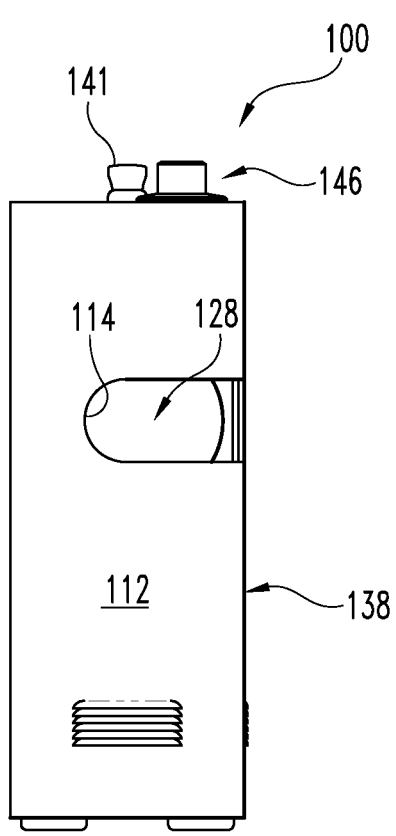
FIG. 2A is a side view of the device of FIG. 1A.
Figure 2B:
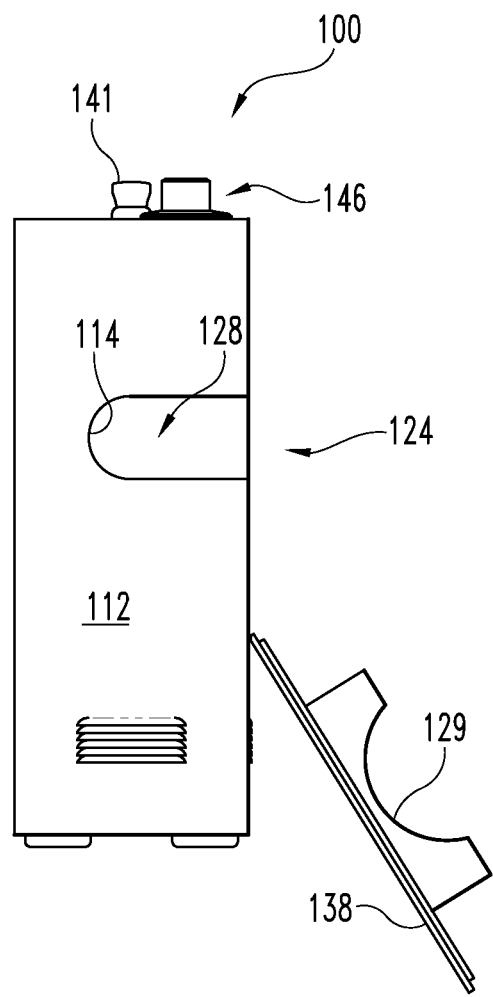
FIG. 2B is a side view of the device of FIG. 1B.
Figure 2E:
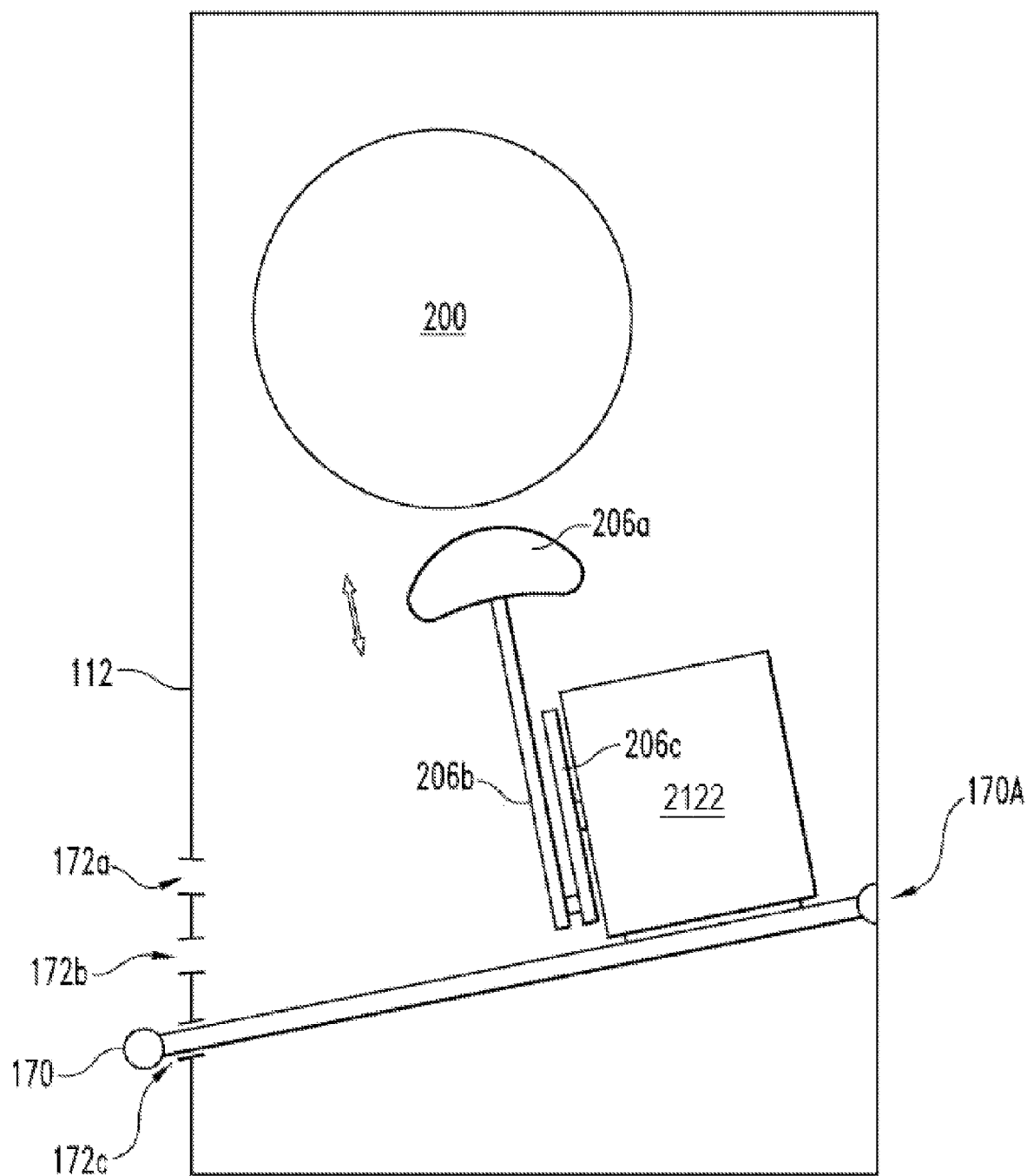
FIG. 2E is a side view, partially cut away, of an alternative device.
Figure 5:
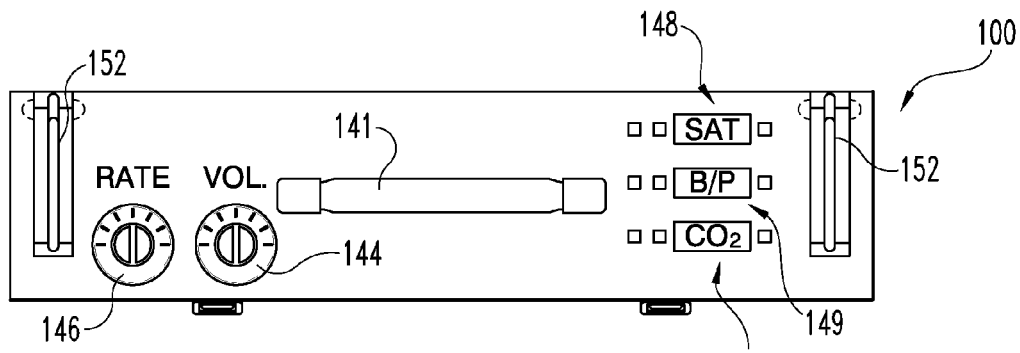
FIG. 5 is a top view of the device of FIG. 3.

With reference to FIG. 5, an optional adjustable volume controller 144 may be included providing operator adjustment of the magnitude of the squeezing of the mechanical compression squeezer to adjust the volume of air/gas per cycle through the flexible self-inflating resuscitator squeeze bag assembly 102. Such controller is also illustrated schematically in FIGS. 9 and 10. Optionally, the adjustment of squeezing may also, or instead, be done mechanically. One example is illustrated in FIGS. 1E and 2E. A handle member 170 and associated platform with hinge 170A may be selectively positioned by movement along slot 171. The section may be continual, or may be discreet such as by predetermined position slots 172a, 172b, and 172c (with more or less such positions). The platform that may be moved may support motor 2122 and wheel/crank 206c and arm 206b to move member 206a closer and/or further from bag 200, thereby adjusting the amount of compression per cycle.

Figure 9:
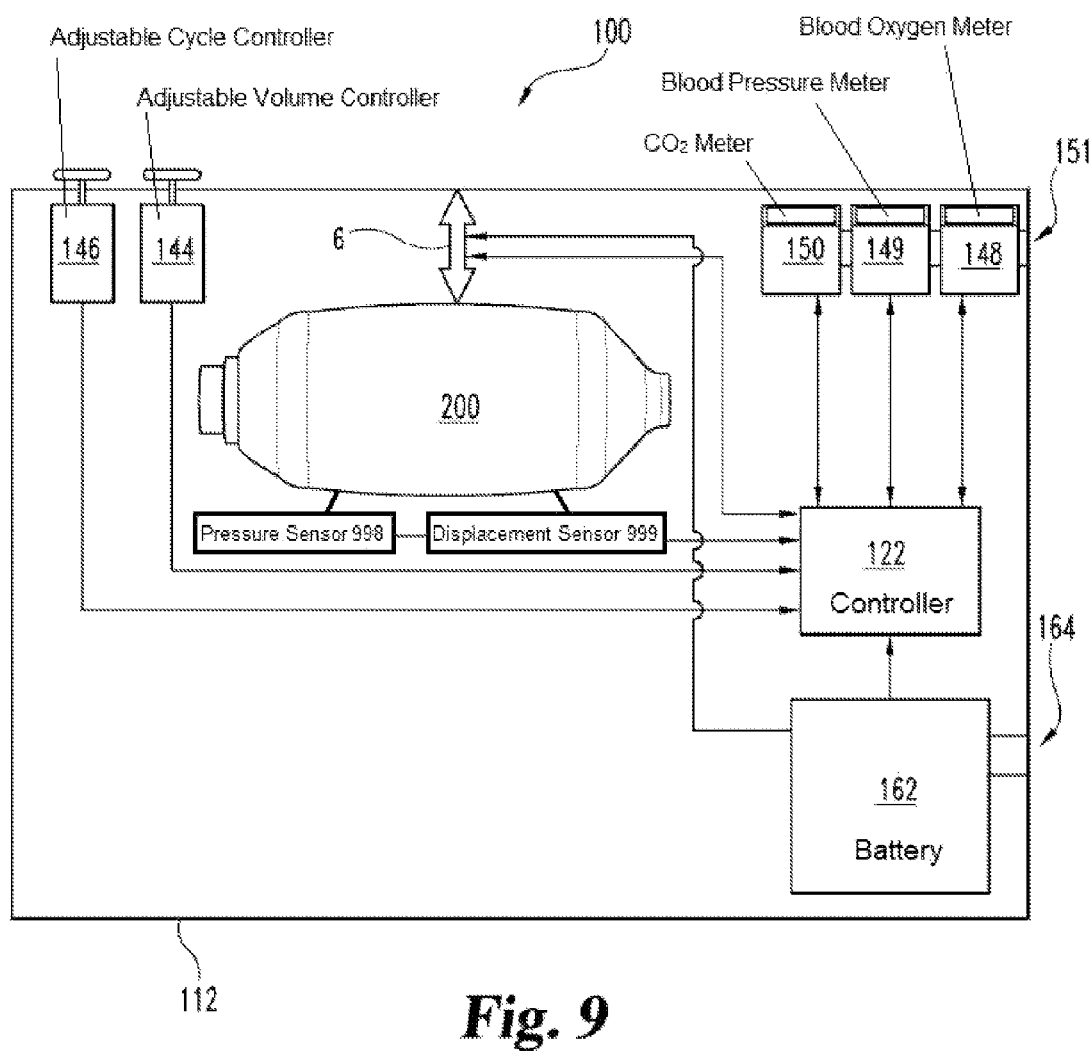
FIG. 9 is one example of a schematic view (not to scale) of optional electronics.

Furthermore, the optional feature of an adjustable cycle controller 146 or 246 (FIG. 1E, 10) or 346 (FIG. 11A) may be included, providing operator adjustment of cycle frequency of the mechanical compression squeezer (see FIGS. 5, 9). Such rate controller may optionally be expressed as the rate or cycles per minute.

Also referring to FIGS. 5 and 9, one or more of optional built in electronic blood-oxygen level sensor 148, $CO_2$ meter 150, and/or blood pressure meter 149, including read out(s) be provided as well.

Another optional feature is other forms of read out devices. These, in addition to meters, may including lights (LED or otherwise) and/or audible alarms. For example, these may include warning indicators for too low a pressure (see light 348 in FIG. 12), too much pressure (see light 349 in FIG. 12) in bag 200 and/or otherwise. This may be monitored by pressure monitors measuring the amount of squeezing by the actuator or otherwise. These optionally may be meters as previously discussed, with or without lights and/or audible alarms if safety thresholds (high and/or low) are exceeded, such as indicator 250. Other indicators may include indicator 248 (see FIGS. 1E and 10) indicating that bag compression has begun. Such readouts may include, for example, a low battery indicator 350 (see FIG. 12), or for example a readout such as light 249a (see FIG. 1E) that is synchronous with the squeezing cycles to give the user a visual and/or audible indication of the rhythm of squeezing of the bag.

Figure 3:
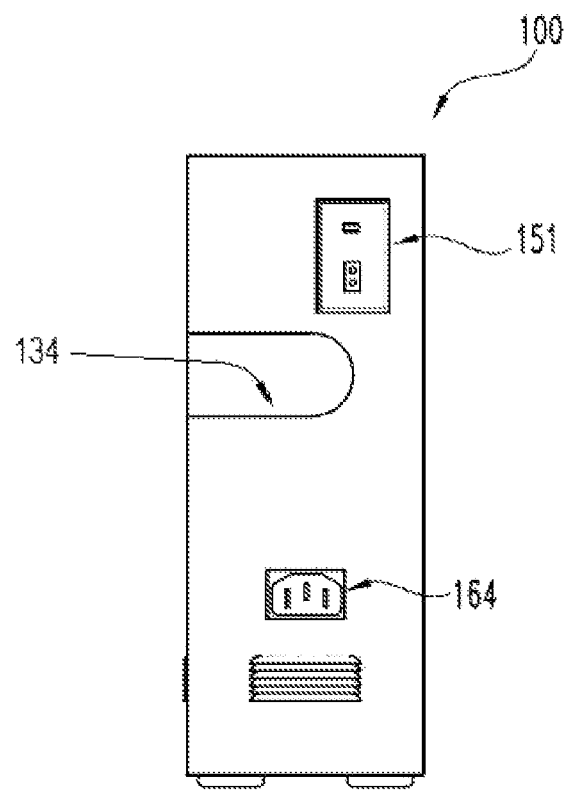
FIG. 3 is a side view opposite the side shown in FIG. 2A.
Figure 7A:
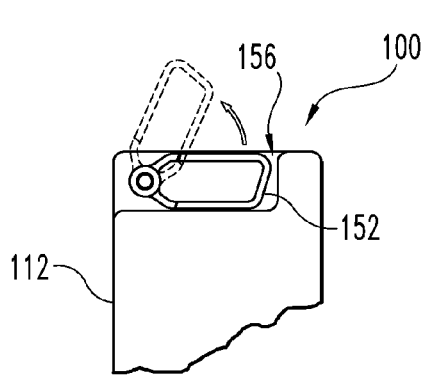
FIG. 7A is a partial cutaway view showing a recessed hook.
Figure 7B:
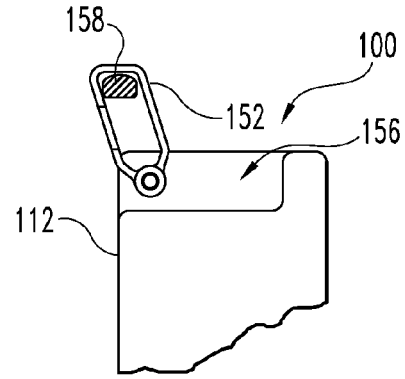
FIG. 7B shows the device of FIG. 7A with the hook out of the recess and hooked on a bedrail.
Figure 8:
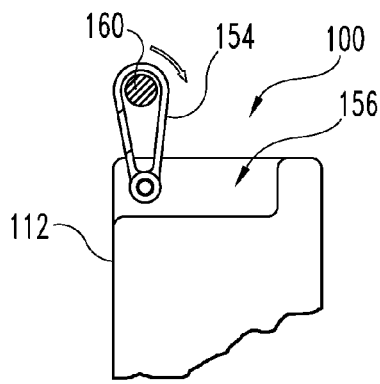
FIG. 8 shows an alternative version of the hook shown in FIG. 7B.

Another optional feature is the use of mounting structures, including without limitation hooks. For example, preferably these may include recessed hooks adapted to hang the housing 112 off a hospital bedrail. For example, with reference to FIGS. 7A, 7B and 8, recessable hooks 152, 352 (see FIGS. 11A, 3M) and 154 are illustrated. These may be recessed (see FIG. 7A, 11A) in a recess 156. These may be adapted to hang off of a hospital bedrail 158 or 160. As such, such hooks may optionally comprise open hooks, or as illustrated spring-loaded carabineer-type hooks. Optionally, they may pivot on an axis to swing up for hooking on the bedrail or other structure (such as a hanging structure in a helicopter or ambulance, or otherwise), or alternatively be pivoted down into the recessed mode.

Preferably, the device 100 in the housing 112 or device 300 is portable such that it will fit in a vehicle, such as a helicopter or ambulance, and optionally, but preferably, includes a battery 162 (see FIG. 9) for providing power to one or more power actuators. Note further that the battery or other power source (such as AC and/or DC power) may provide power to controller/microprocessor 122 and other electrical components in the device. Note further that preferably, the battery is replaceable, preferably easily and quickly replaceable for field operations. Also, the battery may include a recharger including a recharger fitting 164 (see FIG. 3) in the housing. An on-off switch, such as switch 361 may be provided.

FIG. 9 illustrates one example of a schematic layout of a portion of the illustrated device. Housing 112 may include squeeze bag 200. The one or more mechanical compression squeezers are diagrammatically illustrated as 6. Controllers 144 and 146 as previously described provide input, as indicated by the input arrows, to control controller/microprocessor 122.

Controller 122 may receive input and/or provide controlling output to squeezer 6, both in terms of cyclical frequency as well as squeezing volume, or both, or neither, as previously described. Optionally, one or more sensors may be placed on the compression squeezers and/or the outside surface of the flexible self-inflating resuscitator squeeze bag. For example, such sensors may detect pressure and/or displacement. As shown conceptually in FIG. 9, pressure sensor 998 may be used to correlate to the amount of back pressure in the patient's lungs. Similarly, a displacement sensor 999 may correlate to the volume of air pushed or forced into the patient's lungs. By providing such optional sensors and feedback, the controller/microprocessor 122 may receive data input therefrom. Optionally, such data input may be used to fully or partially automate and/or self-adjust the amount of squeezing pressure and/or volume, such as to accommodate the various physiologies of various patients. Controller/microprocessor 122 may also provide input and/or output to blood oxygen, $CO_2$ meter and/or blood pressure meters 148, 149 and/or 150 as well. Optionally, feedback from the meters to the microprocessor/controller 122 may be used alone or in connection with pressure and/or volume feedback sensors and/or pressure and/or volume controllers, discussed above.

For example, if the blood oxygen and/or $CO_2$ level for a patient, as detected, falls below the predetermined level, the controller/microprocessor 122 may be programmed to self-adjust to increase the cyclical frequency, thereby passing more air/gas through the patient's lungs, hopefully increasing the blood oxygen level to the desired threshold level.

Figure 10:
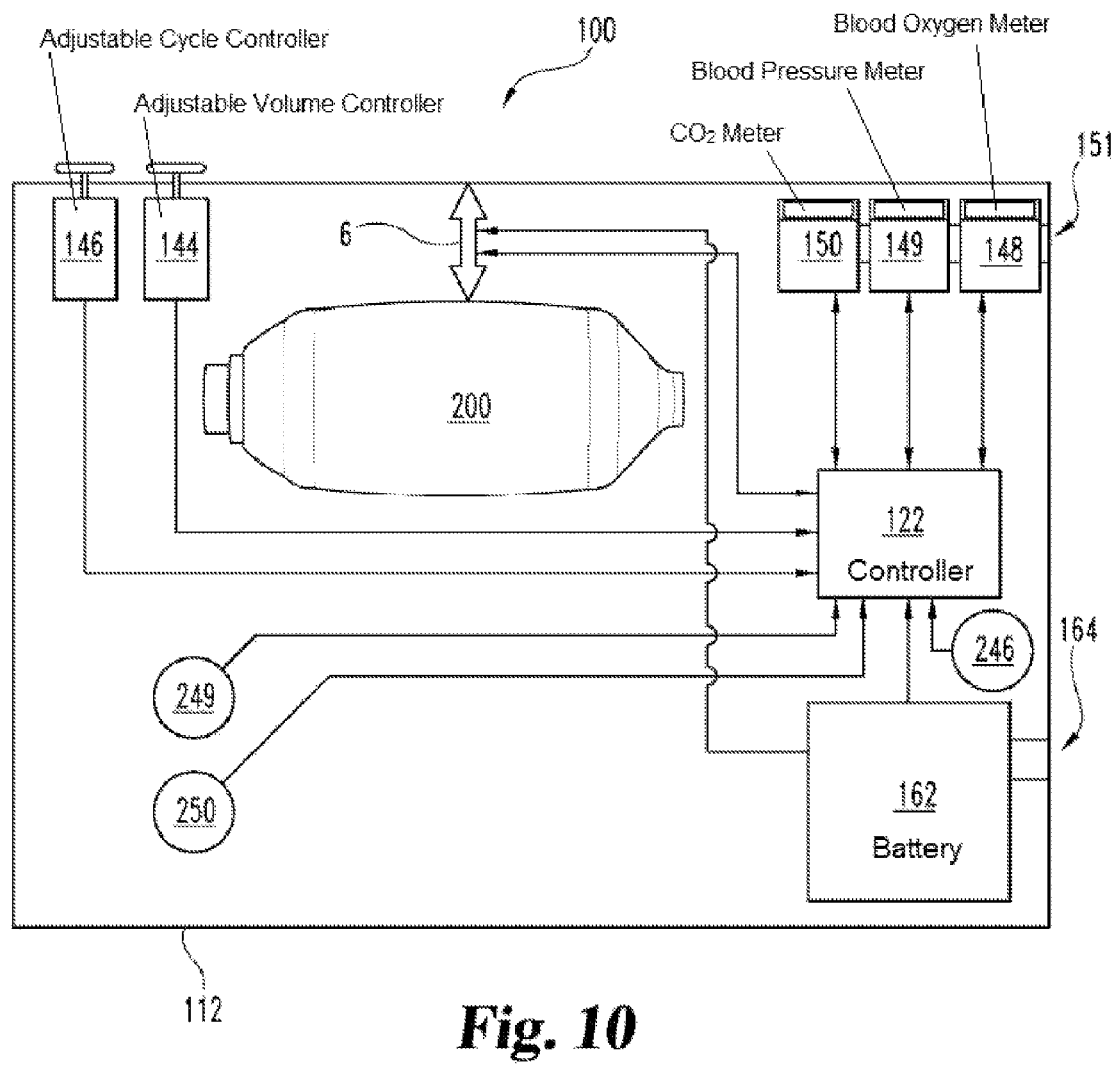
FIG. 10 is another example of a schematic view (not to scale) of optional electronics.

Note also that the meters 148, 149 and/or 150 preferably receive their input via plug-in fitting 151, whereby blood pressure detectors attached to the patient and/or blood oxygen level detectors attached to the patient are plugged into device 100. Typically, the $CO_2$ measurement is taken from or in tube 108 and/or attachment 136. FIG. 10 is like FIG. 9 with the addition of input and/or output devices 246, 249 and 250 previously discussed.

As mentioned, FIGS. 2E, 6A-6J, and 13B and 13C are merely examples of types of compression squeezers that may be utilized, as illustrated or as modified, that are combined with each other.

Figure 6A:
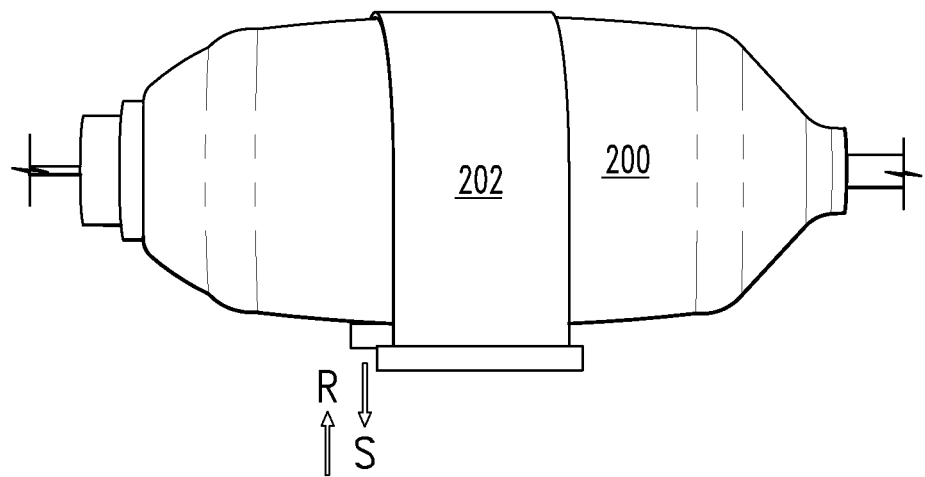
FIGS. 6A-6J illustrate various examples of mechanical compression squeezers.

For example, FIG. 6A illustrates the use of one or more straps, such as strap 202 wrapped wholly or partially around squeeze bag 200. Cyclical tension and/or pulling on strap 202 causes squeezing S, whereas converse releasing of such pulling/tension allows releasing R of the squeeze bag. Such pulling may be effectuated by any type of mechanical, pneumatic, hydraulic or other action, including motorized winders, reciprocated solenoids or other plungers, gears or the like.

Note that with respect to strap 202 in FIG. 6A, this may pull a hoop stress on the outside of the squeeze bag. Another alternative arrangement would be that member 202 could itself be an inflatable bladder, filled with compressed gas and/or liquid, thereby effectuating hoop stress and/or other squeezing on the squeeze bag. Note also that the member 202 may preferably be conveniently coupled and uncoupled (see e.g., latch 342) to allow convenient drop-in insertion of the squeeze bag within the housing, with subsequent confinement of the squeeze bag by wrapping the member 202 or 329 around it. Optionally, one or more handles, such as handle 141 or handle 341, may be provided on case 112, such as to make it more conveniently portable.

Figure 6B:
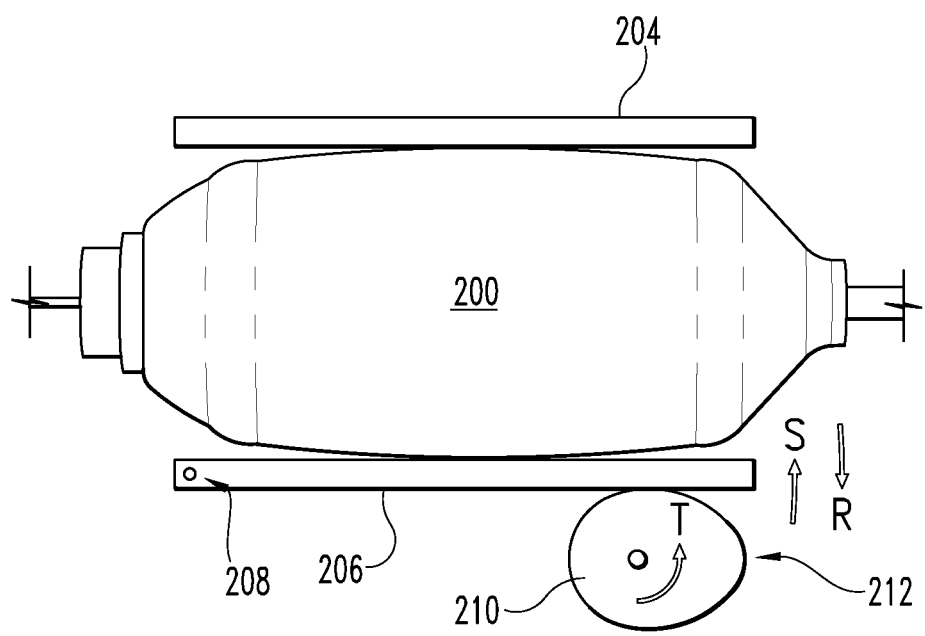

FIG. 6B illustrates an alternative embodiment in which squeeze bag 200 may be positioned between one or more members, optionally but preferably rigid. Note that one or more of such members may be stationary or moveable, although preferably at least one, if not both are movable. For example, as diagrammed in 6B, member 206 is moveable but pivoting around pivot 208. A rotating cam 210 is provided, which may rotate or turn in the direction indicated. Cam 210 can include one or more lobe(s) 212 which, when turned in engagement with member 206 causes squeezing S, whereas disengaging of lobe may allow releasing R. Note that optionally, but not required, member 206 may be biased, with springs, counter-rotation cams, or otherwise, in the released position. The same may be true of other examples described herein. Note although members 204 and/or 206 in these particular examples are shown separate from the housing, they may be wholly or partially part of the housing. For example, optionally member 204 may simply be a wall or portion of the housing itself. Note that although as illustrated, the axis of pivot 208 is transverse and skew to the central longitudinal axis of the flexible self-inflating resuscitator squeeze bag assembly 102, it may be any orientation including parallel.

Figure 6C:
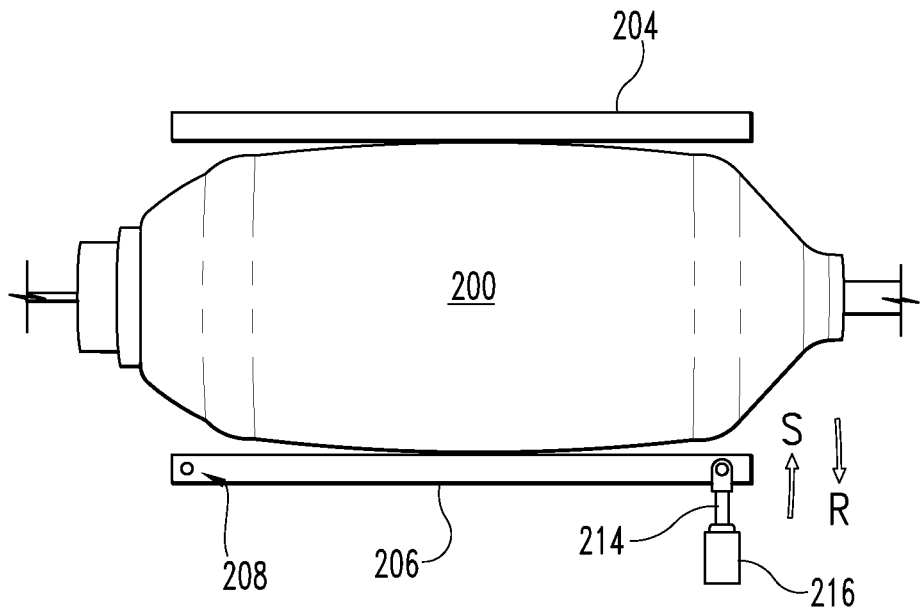

FIG. 6C illustrates member 206 as moveable by a reciprocator, for example having an extendable arm 214 movable (telescopically or otherwise) with respect to element 216. In such case, extension upward causes squeezing S as illustrated, whereas movement in the opposite direction causes pivoting of member 206 around pivot 208 back to the release R direction/position. Such reciprocating actuator can be electrical, solenoid, servo, worm gear, rack gear or other such operation including for example wheel and/or crank systems (see e.g., FIGS. 2E, 6I, 6J, 13B, 13C), and preferably as before powered with a powered actuator such as a motor, hydraulics, pneumatics or otherwise.

Figure 6D:
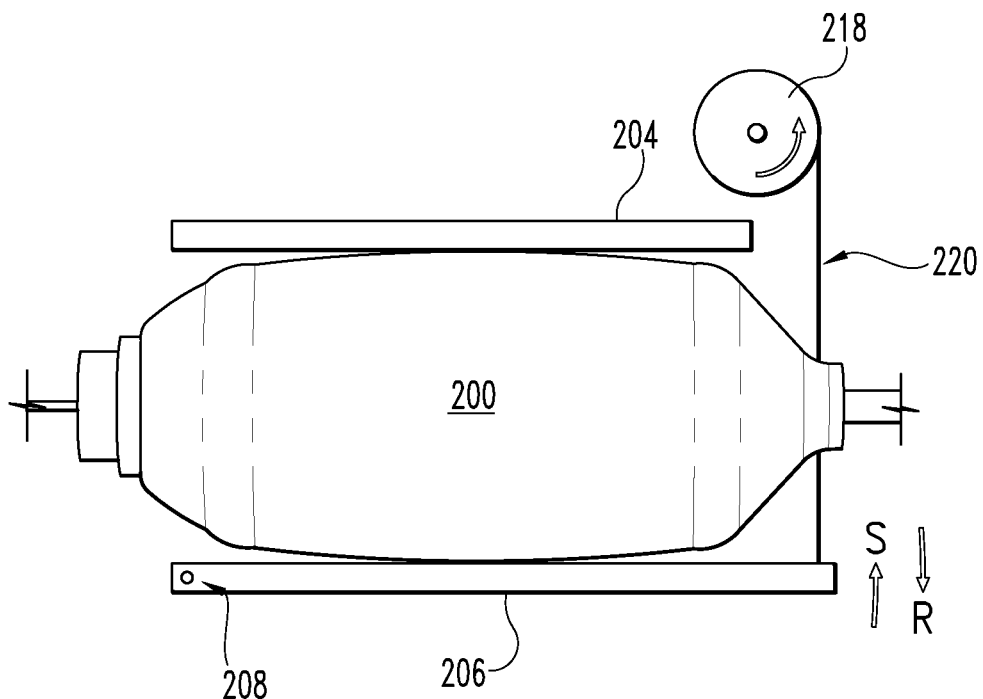

FIG. 6D illustrates a version using a winder that turns as indicated by the arrow, winding, and thereby exerting tension on tension member, such as cable 220 or cord or otherwise. When it is wound in tension in the arrangement illustrated, member 206 pivots around 208 and squeezes in the direction S. When winder 218 releases, the bag may be released in direction R. Again, spring or biasing may be used, or alternatively an opposite-directed counterwinding mechanism or cam or otherwise may be used to effectuate releasing R.

Figure 6E:
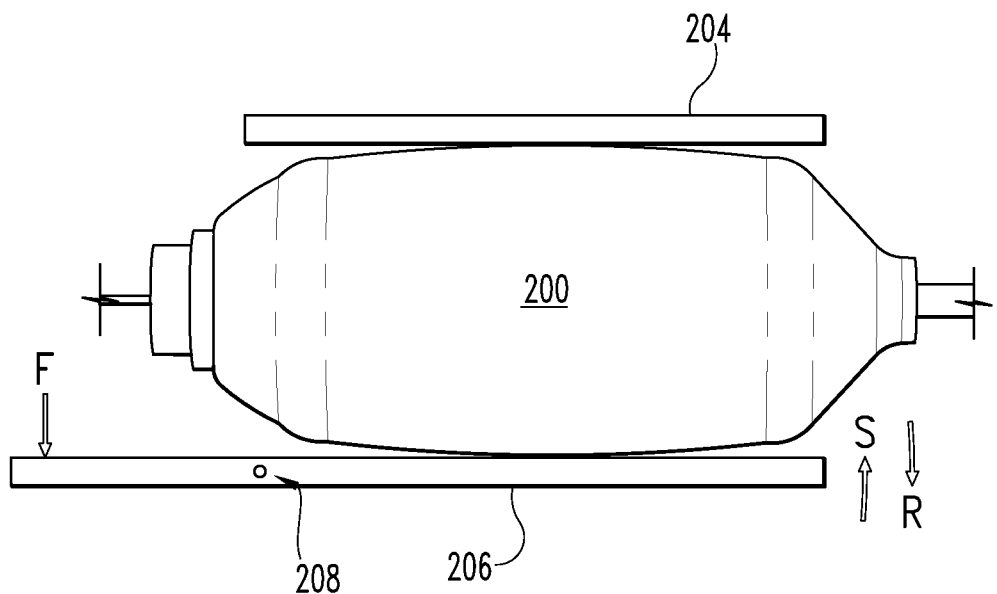

FIG. 6E illustrates the use of force F on an opposite side of pivot 208, to create a fulcrum action for squeezing S. As such, any of the previously or subsequently mentioned actuators, cams, tension members, and otherwise may be directed on the opposite side of pivot 208, in those situations when a pivot is used, to effectuate squeezing. Conversely, a direction opposite to force F may be used at the location indicated at force F to effectuate releasing R. Note further that all of the actuator mechanisms described in this document may be concurrently imparted on more than one member, such as being imparted on both member 204 and member 206 simultaneously.

Figure 6F:
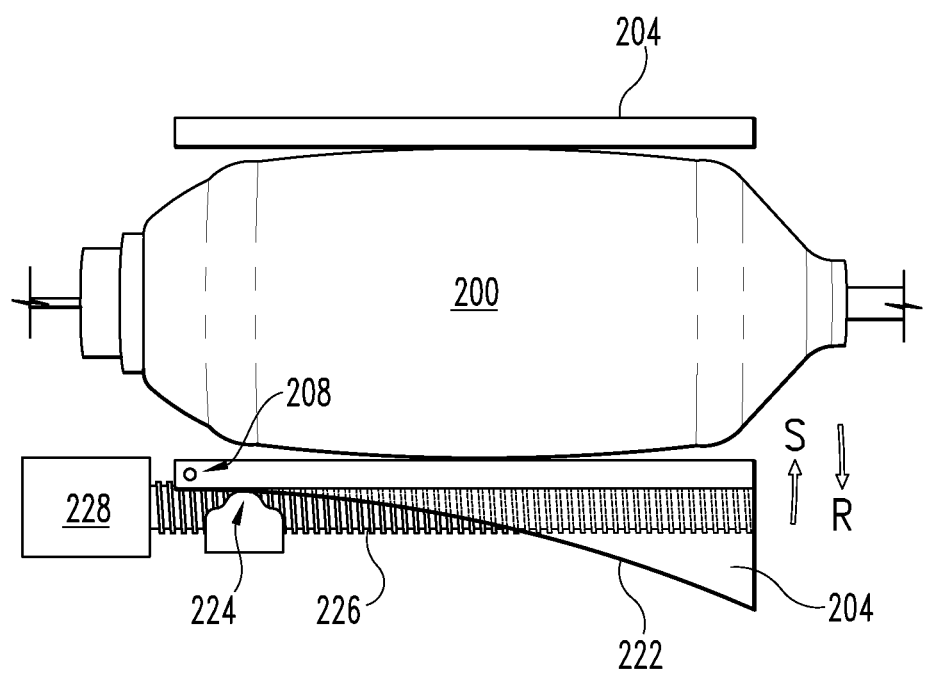

FIG. 6F indicates an arrangement with a cam surface 222 and a cam follower 224. Linear movement of the cam follower (for example, left to right) exerts force on cam surface 222, thereby causing member 204 to pivot around pivot 208, thereby effectuating the squeezing S. As one example, cam follower 224 may be moved longitudinally by having threaded engagement with the gear, such as worm gear 226 rotated by gear/motor driver 228. Other arrangements may be included, such as using a gear rack rather than a worm gear and/or gear driving and/or motorizing the follower 224.

While the foregoing examples include pivoting motion, such as pivoting 208, such pivoting is not required. For example, in FIG. 6G, squeezing and/or releasing may be effected by moving one or more of member 204 and/or 206 longitudinally, such as along guides 230 and 232. Squeezing and/or releasing force may be, for example, of the type previously described, and/or pneumatic and/or hydraulic inflation bags or the like.

Figure 6G:
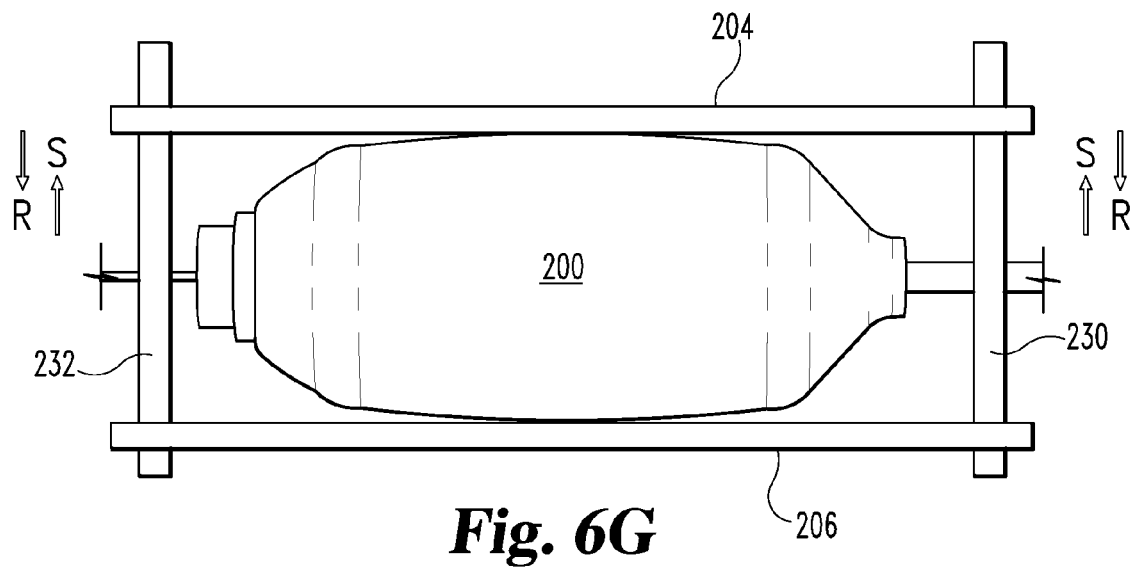
Figure 6H:
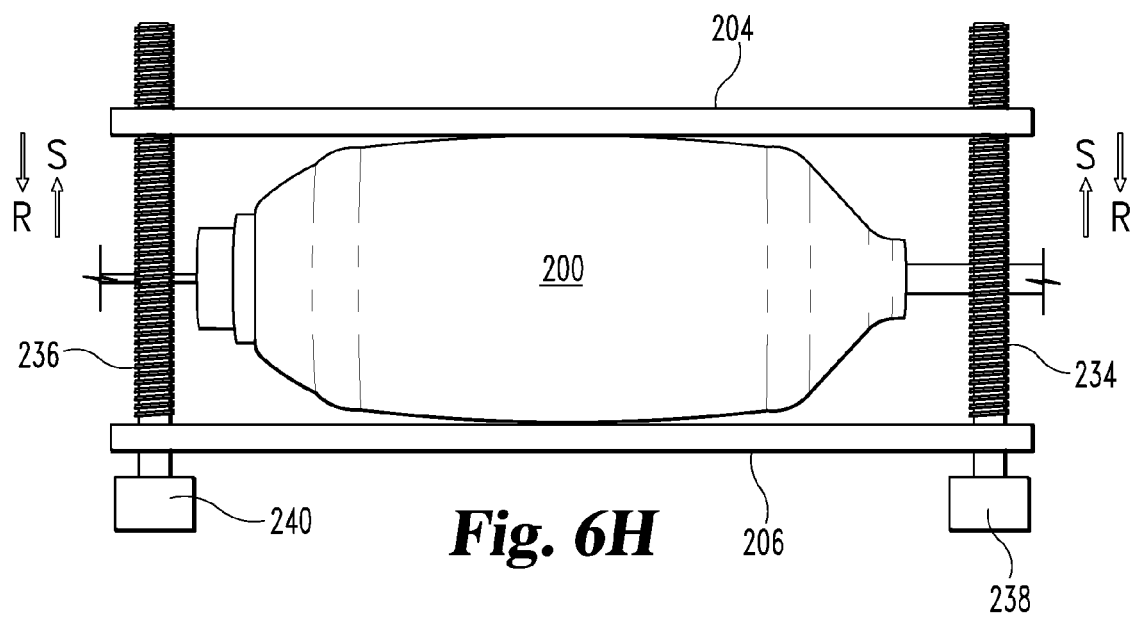

Similarly, instead of sliding guides or rails, such as previously mentioned with respect to FIG. 6G, FIG. 6H describes an alternative arrangement in which gear drives, such as one or more of worm gears like worm gear 234 and/or 236 may be rotated, such as by rotating driver 238 and/or 240, thereby causing squeezing S and/or releasing R of bag 200.

Figure 6I:
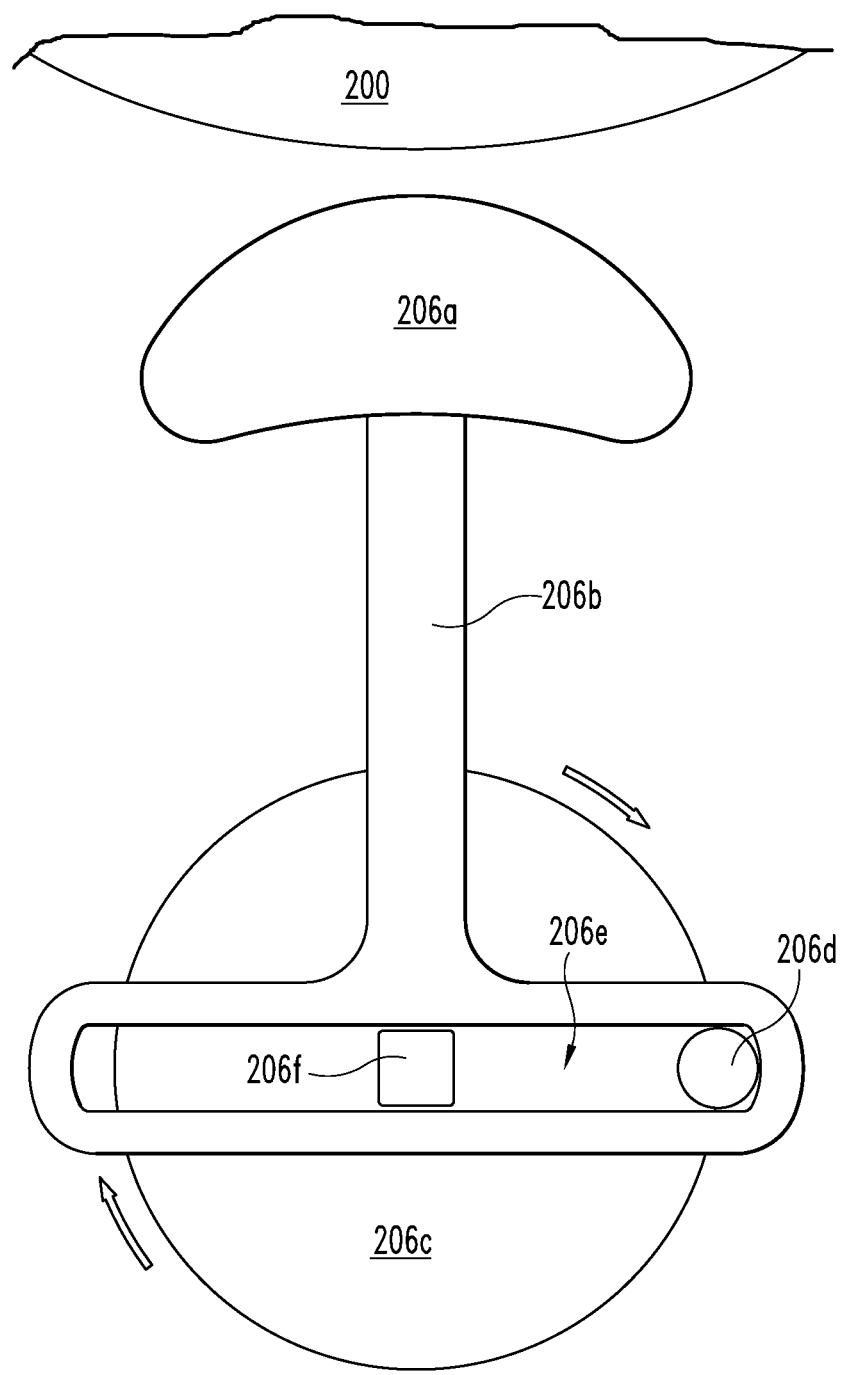

FIG. 6I illustrates another example with member 206a for squeezing bag 200. Member 206a connects to crank member 206b. As illustrated in this particular example, and not by way of limitation, crank member 206b has generally a t-shaped geometry. It may be most any shape. Note also that crank member 206b may optionally include an elongated slot 206e. As illustrated, slot 206e allows for sliding or other movement along the slot of the crank with respect to connection 206d to rotating member 206c. Rotating member 206c may be rotated by any mechanical means, for example, rotational drive 206f may rotate rotating member 206c. Note that in this particular example of FIG. 6I, drive shaft 206f is preferably generally flush with a surface of rotational member 206c. Drive shaft 206f does not slide in slot 206e. Slot 206e provides paused (including slowed) movement in the squeezing motion of 206a. This may occur as connection 206d advances and retreats along slot 206e, typically at the apex and its opposite rotational location.

Figure 6J:
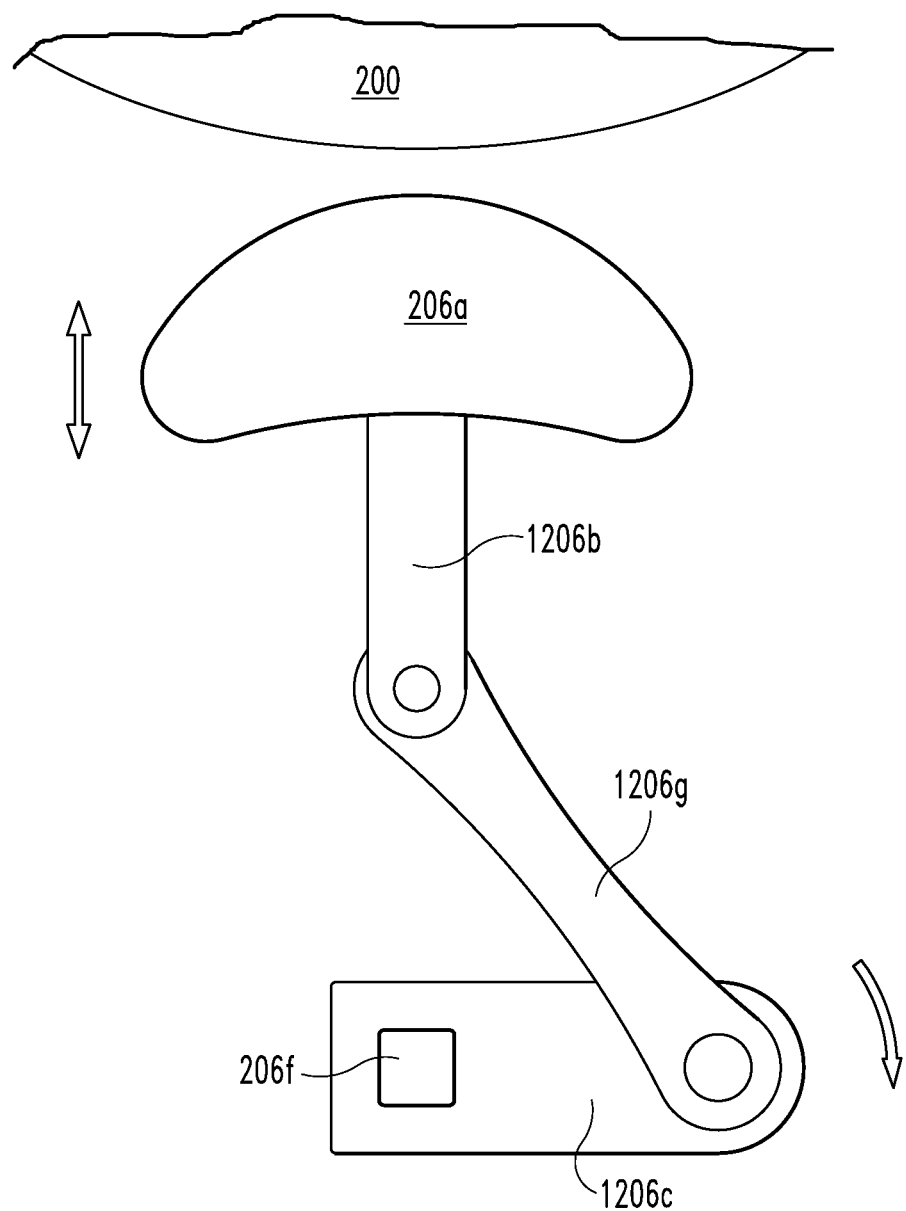

FIG. 6J, like FIG. 6I, illustrates member 206a (or any other squeezer or intermediary part(s)) connected to crank members 1206b and 1206c. Those two members may be pivotally connected to rotational member 1206c which may be driven by shaft 206f rotation as indicated.

Figure 13A:
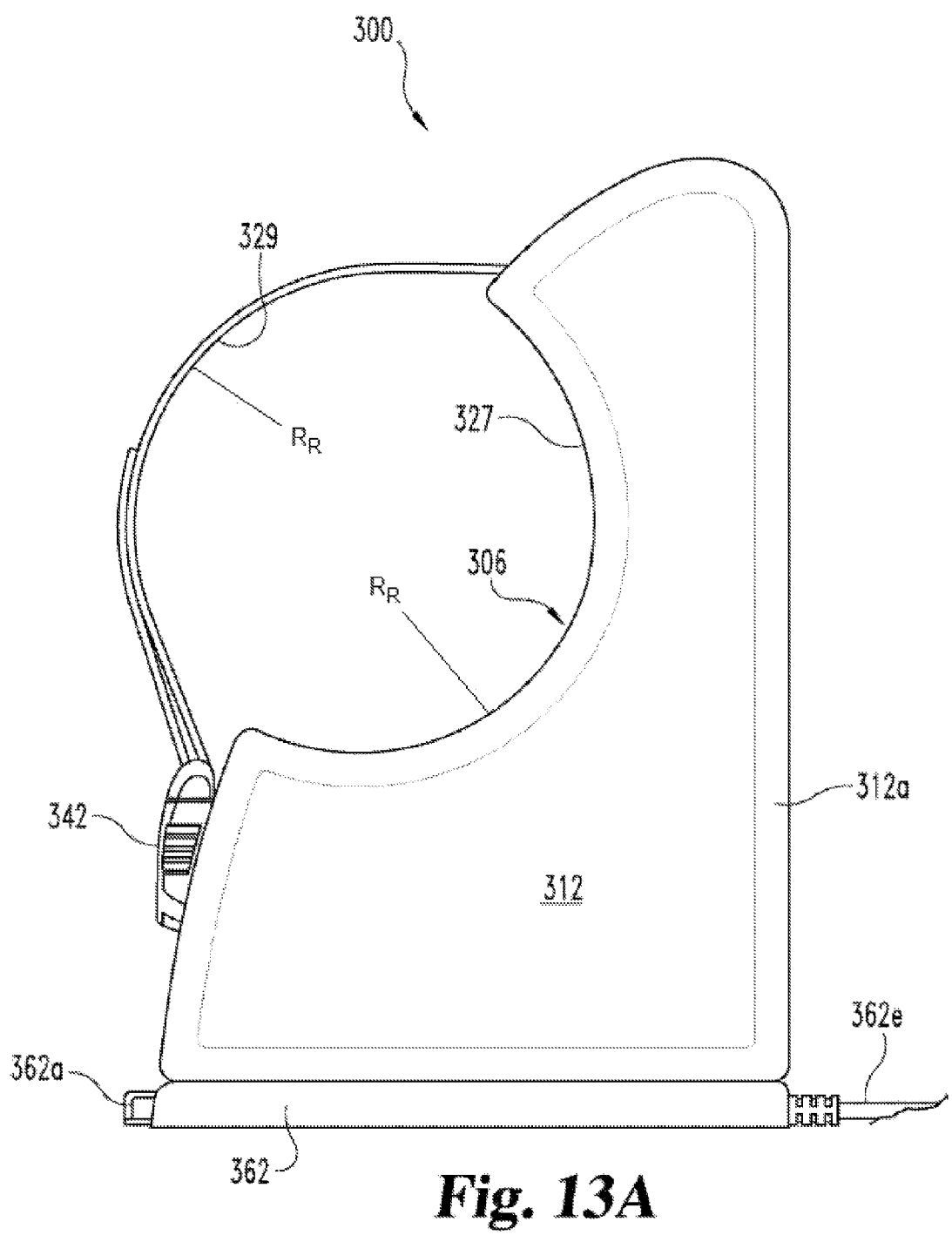
FIG. 13A is a side view of the device of FIG. 11A.
Figure 13B:
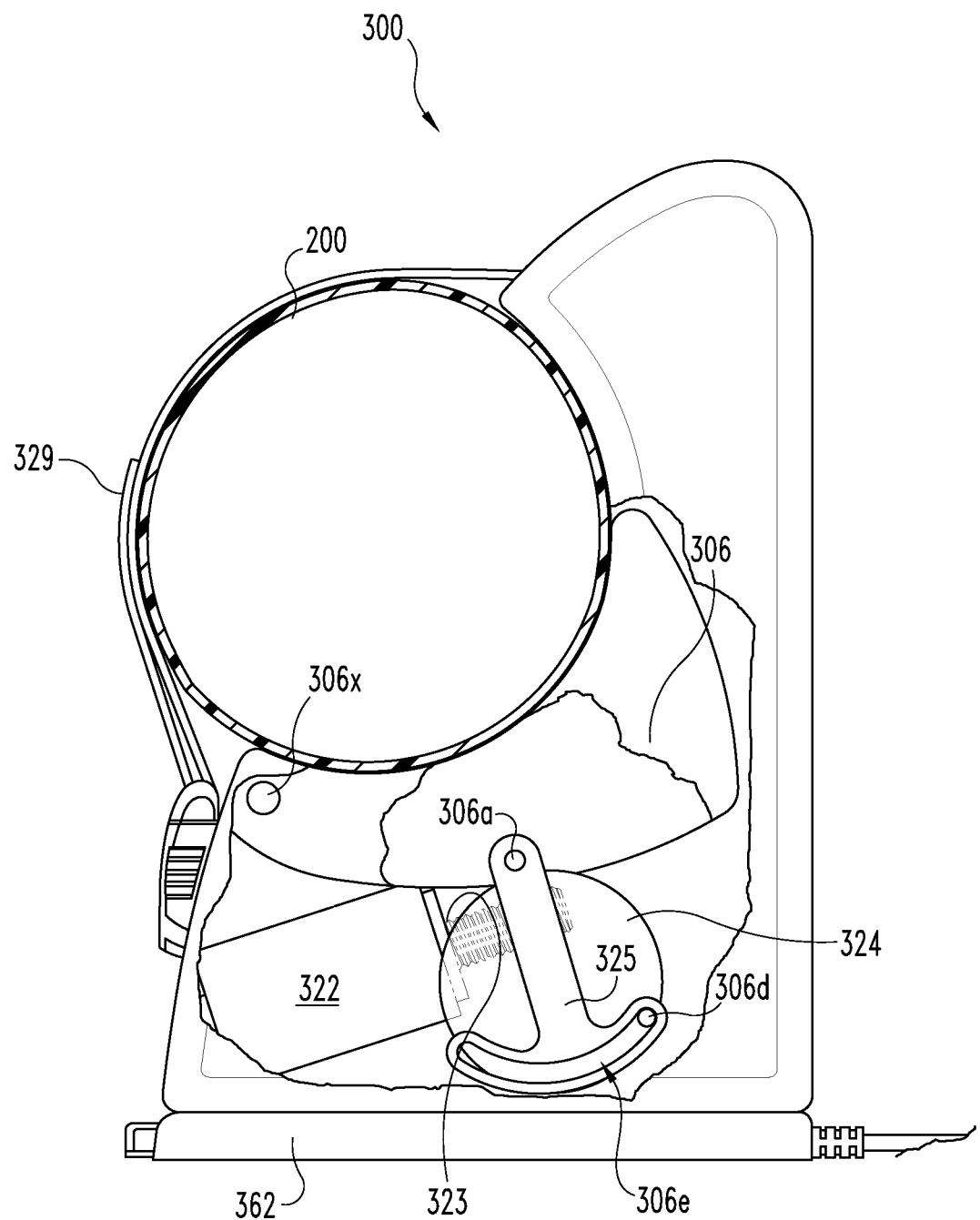
FIG. 13B shows the device of FIG. 13A with bag 200 therein, showing the device and bag partially cut away.
Figure 13C:
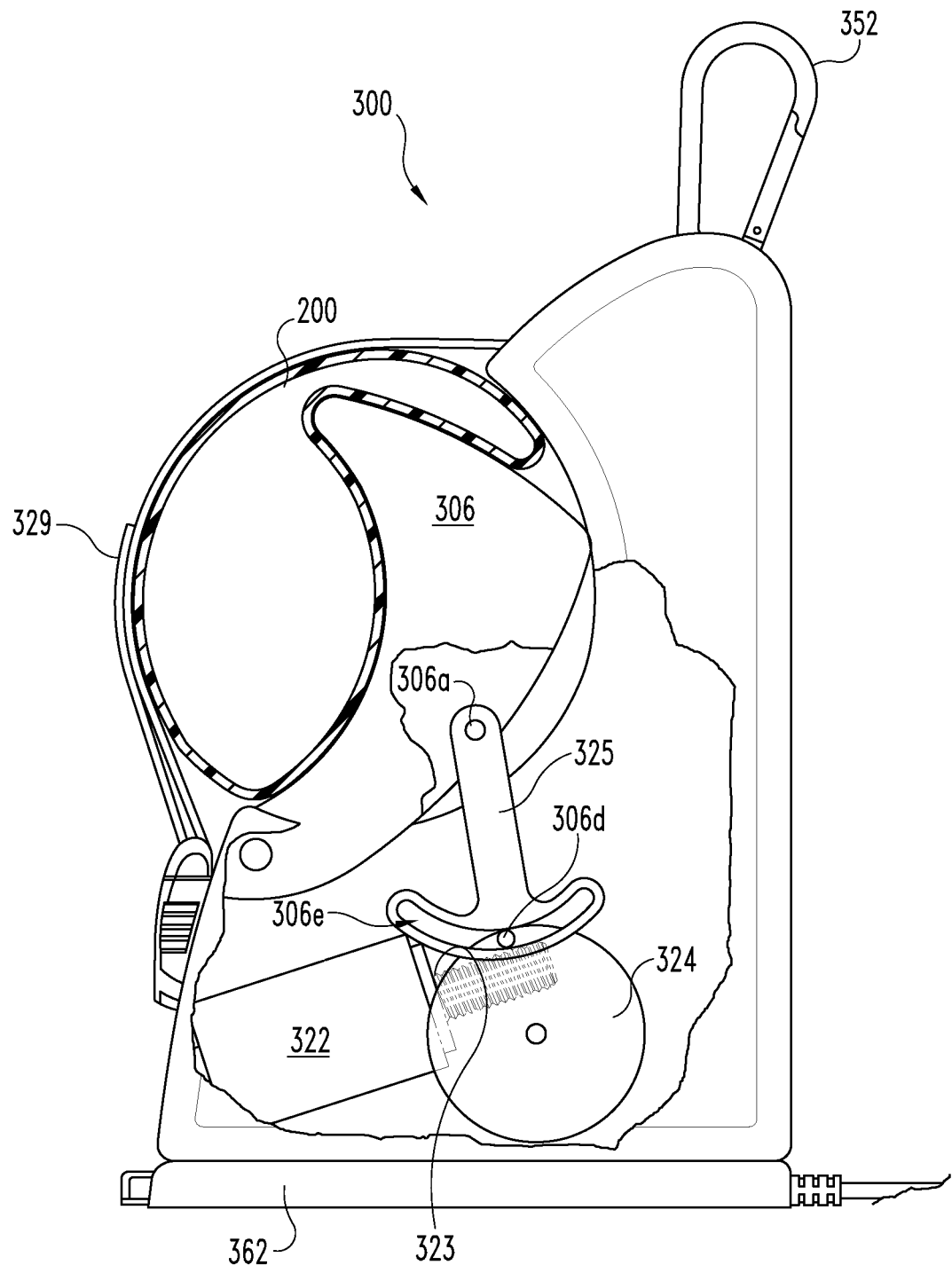
FIG. 13C shows the device of FIG. 13B in a squeezed position.
Figure 14:
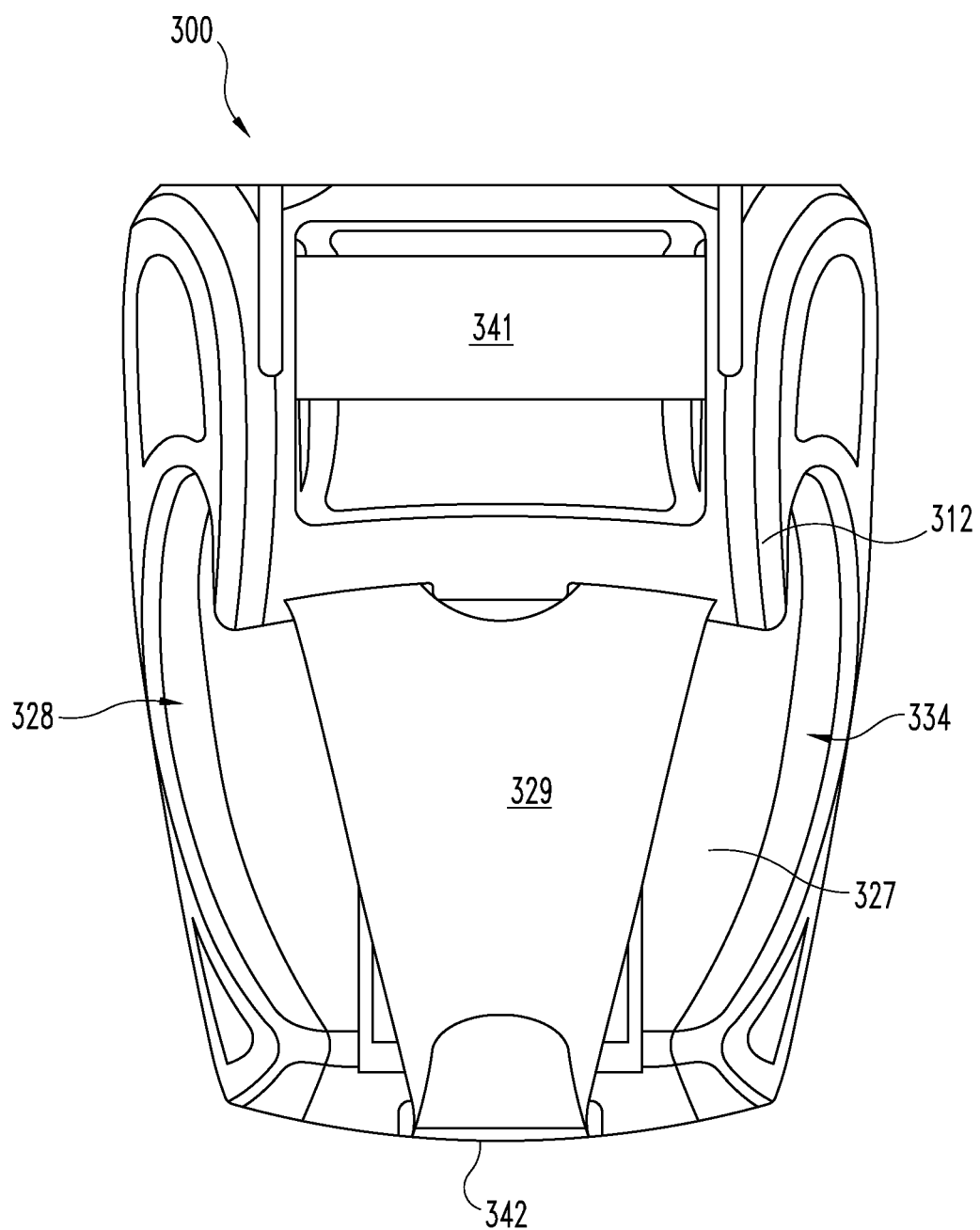
FIG. 14 is a top plan view of the device of FIG. 11A.
Figure 15:
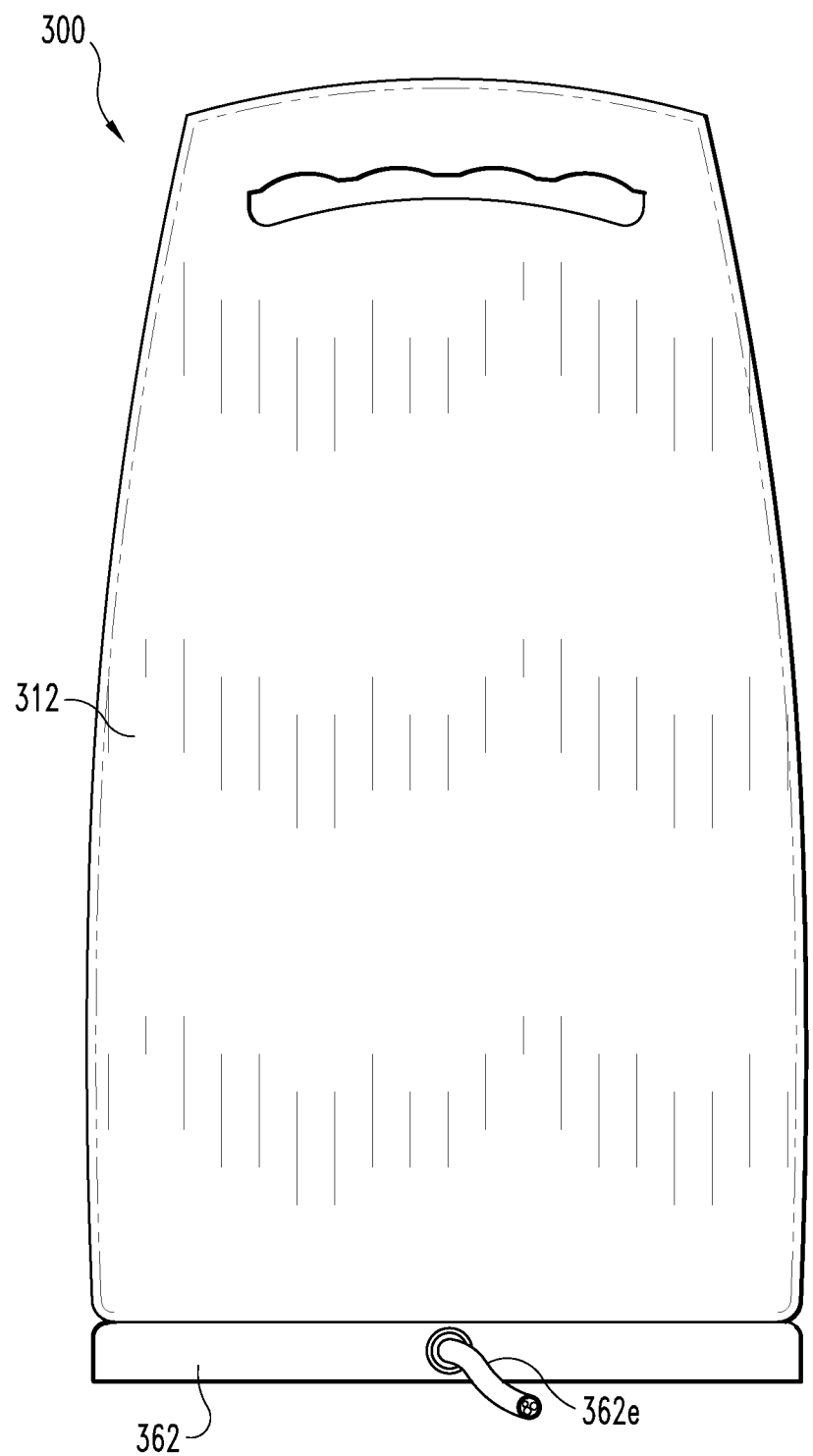
FIG. 15 is a rear elevation view of the device of FIG. 11A.

FIGS. 13B and 13C, which are partially cut away versions of FIG. 13A, show merely an example of a power actuator within a housing. As before, other styles of actuators may optionally be used such as discussed in this patent document. Such a crank arrangement as illustrated in FIGS. 13B and 13C is like the crank arrangement previously described in connection with FIG. 6I. One optional difference, however, is that as compared to the slot 206e (shown in 6I), slot 306e may be curvilinear, such as shown with the curvilinear profile that is a segment of a circular arc. Slot 306e may provide for movement pausing (including slowing, or optionally a full stop pause) of squeezer 306. As illustrated in FIG. 13B, at the downstroke position of crank member 325, connection 306d in the slot is in the most forward advanced position of slot 306e. With, for example, counterclockwise movement, connection 306d advances the forward position of slot 306e up. However, by then looking at the upstroke position shown in FIG. 13C, it is illustrated how 306d is moving backward in slot 306e, and as illustrated is somewhere in the mid-slot region. As the rotational member 324 continues to rotate, the connection 306d will continue to retreat in the slot 306e toward the rearward position of rotational member 324. As can be seen, crank member is connected to mechanical compression squeezer 306 at connection (optionally a pivot) 306a. Thus, as it moves from position FIG. 13B to FIG. 13C, it squeezes bag 200. Moreover, due to the previously described movement, the connection 306d in slot 306e, the squeezing action occurs on the upstroke, but remains paused, at least partially paused/slowed, in the squeezed mode while the connection 306d slides from the forward to the middle to the rearward position in slot 306e. As wheel or other shaped member 324 continues to rotate counter-clockwise, crank member 325 may pull member 306 back out of squeezing bag 200. Also, returning to position slightly prior to what is shown in FIG. 13B, connection 306d will then do the inverse of that previously described, namely advance from the rearward position of slot 306e to its mid-slot region and eventually back to the forward position as depicted in FIG. 13B. As before, this provides pausing at the downstroke and/or as corresponding to the bag 200 being inflated or unsqueezed, or at least partially so. Thus, such pausing can pause with the bag squeezed from the outside and likewise can pause with or as the bag is inflated. Optionally, the duration of the pause and the profile of the pause may be altered by altering the length, curvature, and/or other geometry of slot 306e. Also, it may be altered by having connection point 306d eccentric to the rotational pivotal center of rotating member 324. Optionally, these and/or other mechanically and/or electrically caused movements may be done simultaneously to provide a squeezing profile. Alternatively, rather that such mechanical pausing (e.g., using slot 306e), servo, stepper and/or other electronically and/or pulse controlled motors may effect such pausing.

Note that the rotation of rotating member 324 may be provided by any means as previously discussed. In a particular example of FIGS. 13B and 13C, electric or pneumatic motor 322 is used to drive the shaft 323. Such shaft 323 is preferably geared or otherwise translated to cause rotation of rotation member 324. Other arrangements may be provided, including orienting motor 322 and shaft 323 perpendicular to that illustrated. When pneumatic, motor 322 may be rotational and/or piston and other arrangements may be provided as well. When motor 322 is electric, electrical power may be supplied by batteries, such as for example 362. Alternatively, or in addition to batteries, power may be supplied from power cord 362e (see FIGS. 13A, 17).

Note that compression squeezer 306 as illustrated is pivoting on a pivot 306x (see FIG. 13B) on the left side of FIGS. 13B and 13C. However, other arrangements may be used, including slides, flexible straps or other flexible members, or otherwise. Additionally, as previously described the rotational action of rotating member 324 and/or of any associated crank may be used to provide tension, rather than a compression, to cause squeezing of bag 200. See e.g. FIG. 6A, 6E, 6G, 6D or otherwise.

Figure 17:
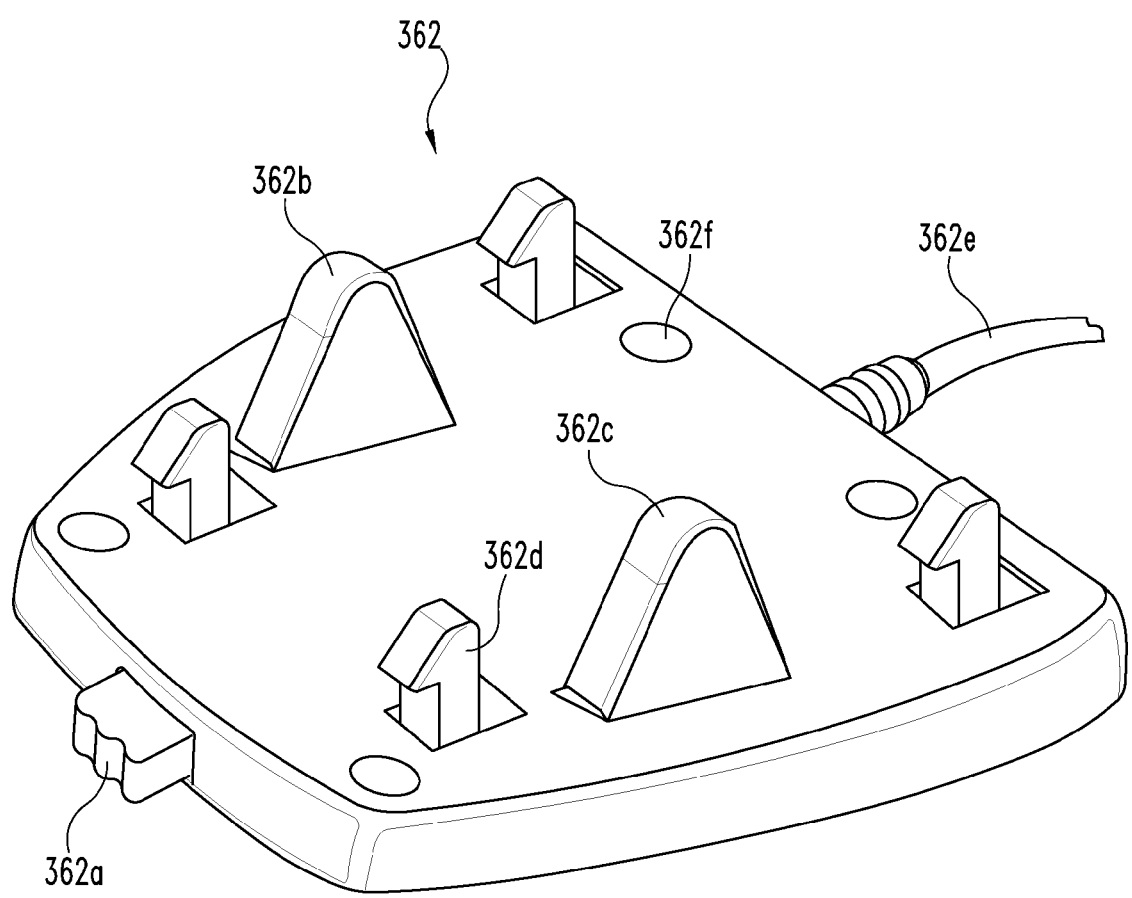
FIG. 17 is a top perspective view of one example of a base forming a part of the device of FIG. 11A.

The example of device 300 shown in FIGS. 11A-17 may be altered in appearance, as well as function, as previously described, although such ornamental appearance is the subject of a separately filed design patent. Optional hooks, such as hooks 352 may be provided, such as shown extended in FIG. 13C. If batteries are part of the device, they may be in the housing. As shown, base 362 may be used at the bottom of the device to provide stability with a low center of gravity. Optionally, this base 362 may be removable as shown in FIG. 17. In that one example, latch hooks such as 362d may provide snap-in attachment to the housing, optionally aided by alignment members such as 362f, which may be pins, recesses, ribs, grooves, or otherwise. Latch lever 362a is one example of a part that can move the latch hooks to disengage with the housing. Preferably two electrical contacts such as 362b and 362c provide a power circuit to the motor and other electrical components of the device needing power. Optional power cord 362e may provide for AC or DC running of the device and/or for recharging of batteries. In this particular example, one or more batteries are provided in the housing, above base 362, and base 362 may provide direct power and/or power to recharge the battery. Another option may be to include some or all batteries in base 362. Also, base 362 may also optionally contain a transformer to drop voltage from an electrical outlet to a lower voltage for battery and/or motor use.

Figure 11A:
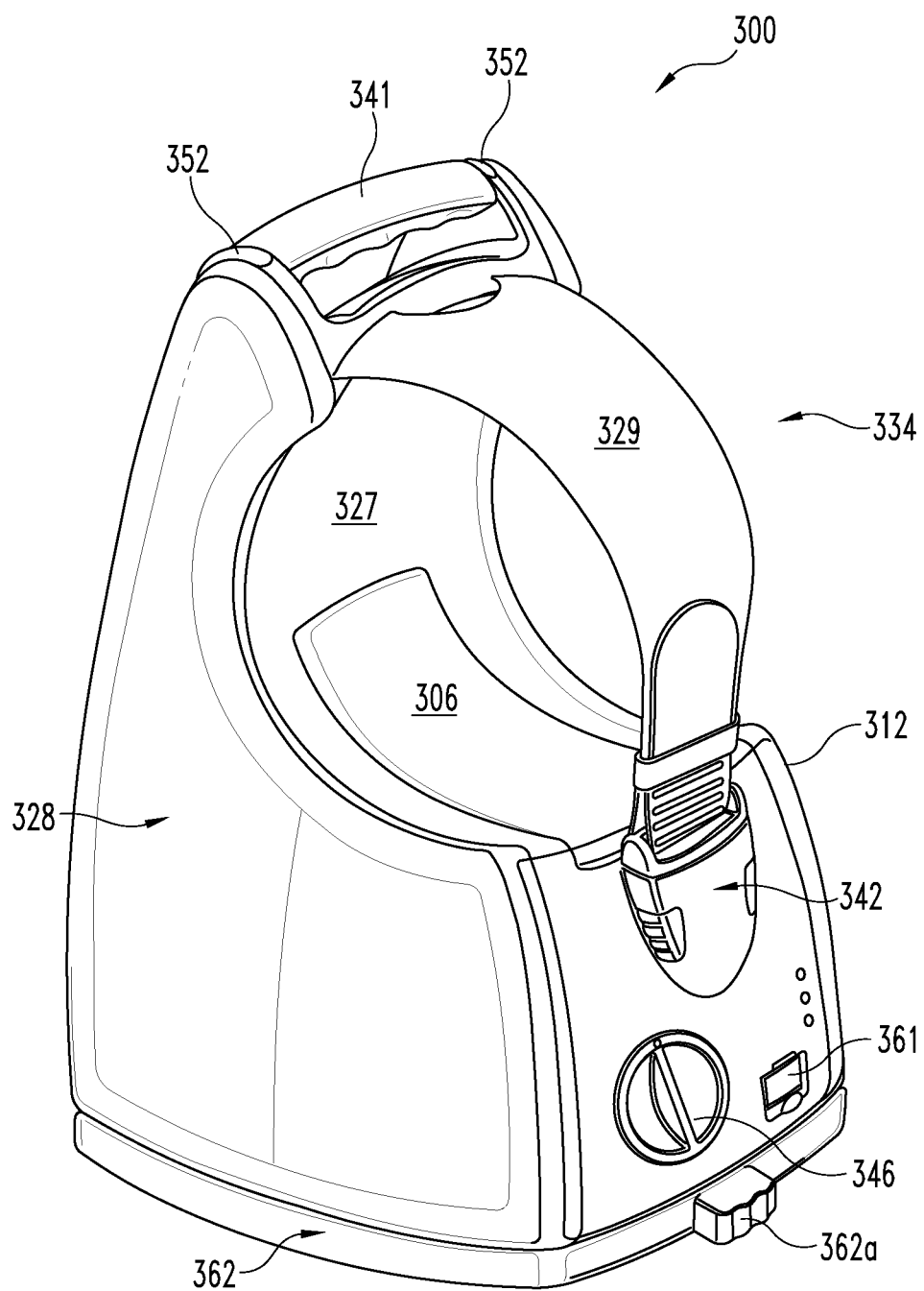
FIG. 11A is a top perspective view of a device according to another example of the present invention.
Figure 11B:
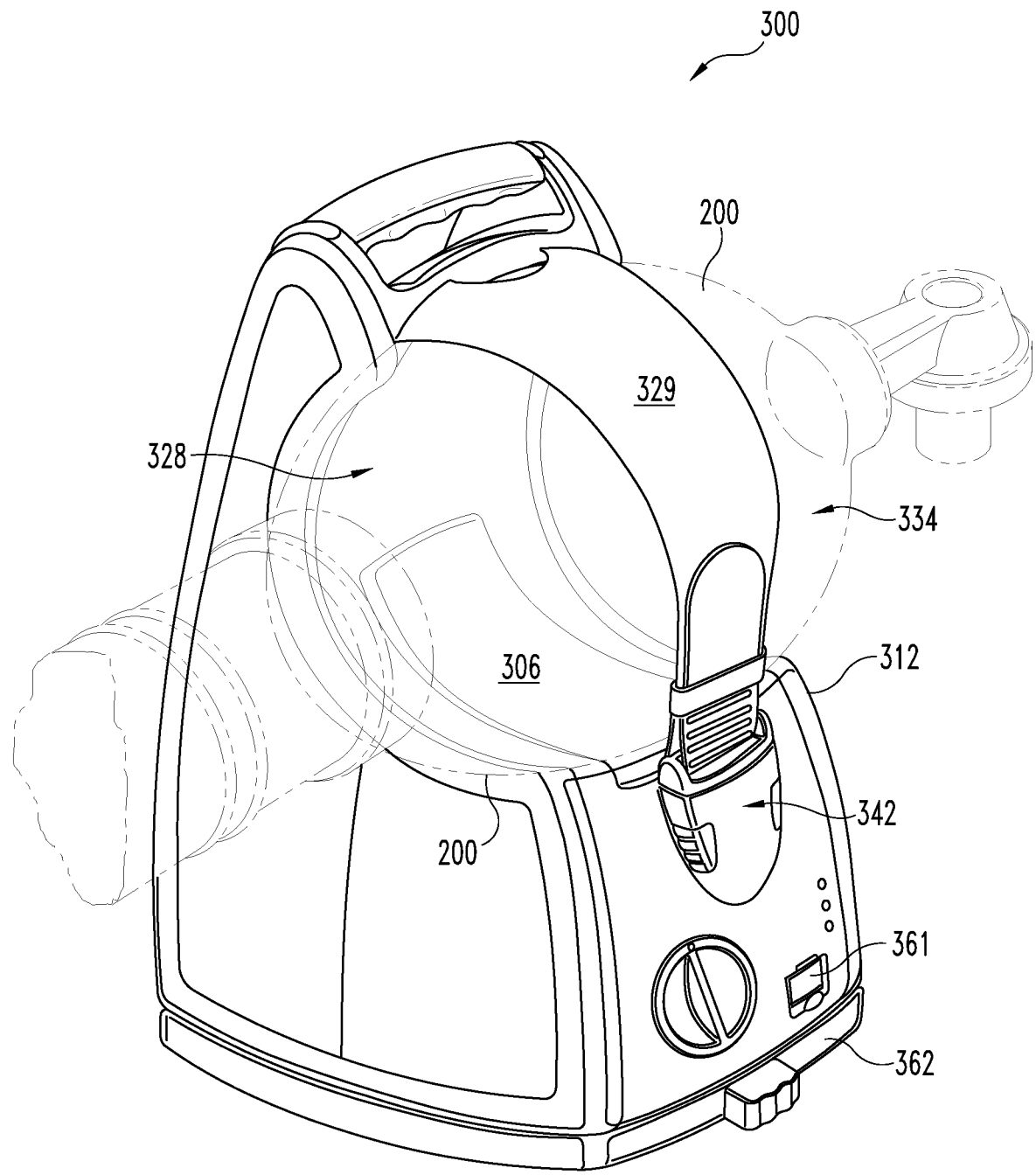
FIG. 11B shows the device of FIG. 11A with a flexible self-inflating resuscitator squeeze bag therein shown in phantom lines.

As mentioned, looking at FIGS. 11A and 11B, lid 329 is shown closed. A latch 324, which may optionally be a buckle or snap or otherwise, may be unlatched to open lid 329. Lid 329 may be rigid (hinged or otherwise) and/or may be flexible, such as a strap. Such strap may be mesh, plastic, cloth, a combination thereof or otherwise. When lid or strap 329 is open, it creates an opening for drop-in insertion and/or removal of bag 200. Ideally, but optionally, there are corresponding curved surfaces between the cylindrical bag 200 and member 306 and/or surface 327 (see FIG. 11A) and/or lid 329 (see FIG. 13A).

The term corresponding curved surfaces will be further explained in view of what has been disclosed in the Figures. When inflated, cylindrical bag 200 is more or less football-shaped as shown in FIG. 11B and as further indicated in FIGS. 1C, 1E, 2C, 2E, 6A, 6B, 6C, 6D, 6E, 6F, 6G, 6H, 6J, 6I, 9, 10, and 13B. Cylindrical bag 200 thus normally has a convexly-curved outer surface, curving convexly in a cylindrical cross-section while also curving convexly about its longitudinal axis as it extends from its first end near collar 118 to its second end near collar 120 as shown in FIG. 1C.

Figure 12:
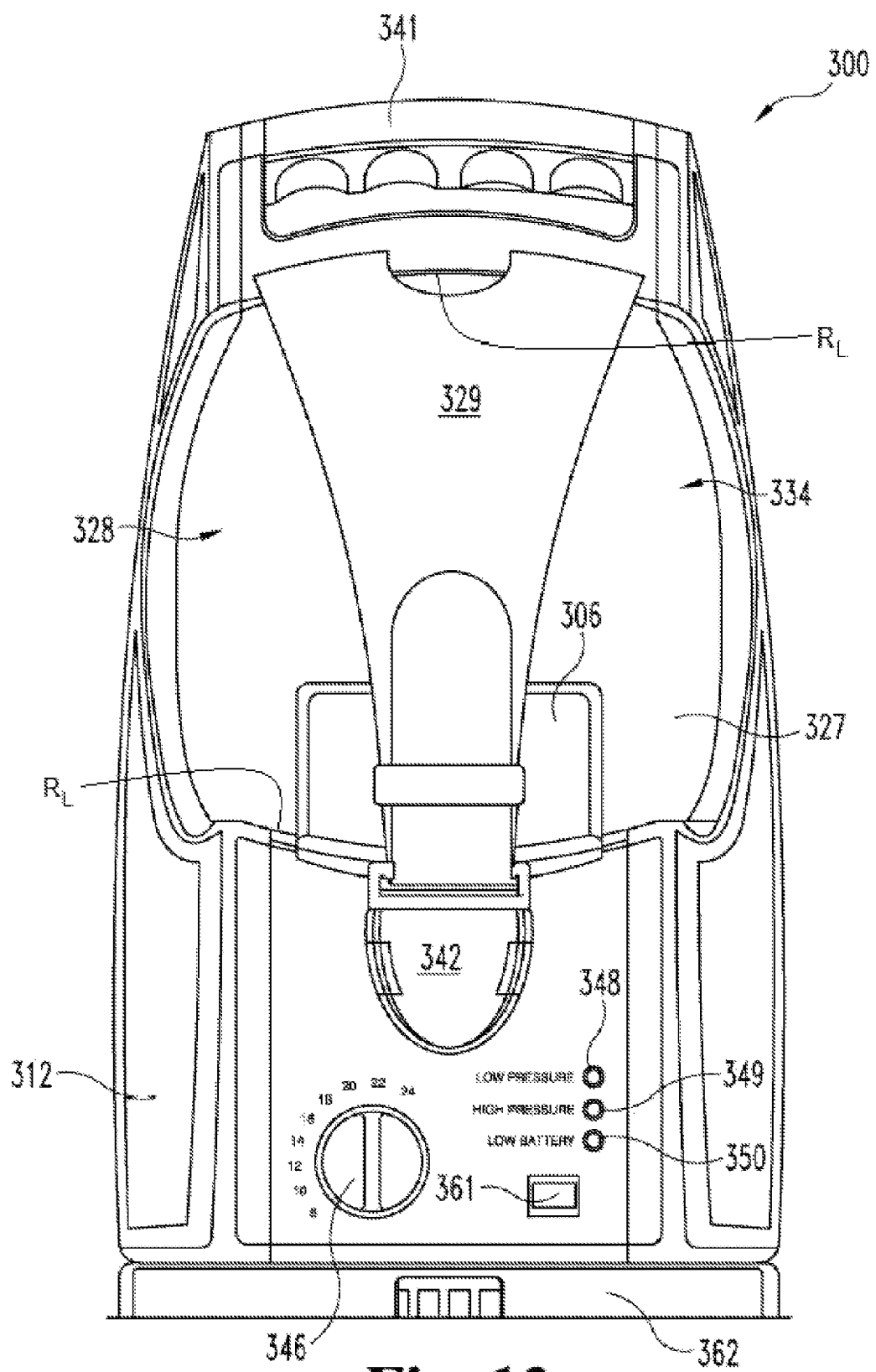
FIG. 12 is a front view of the device of FIG. 11A.

To correspond to the convexly-curved outer surface of the cylindrical bag 200, at least any or all of the following surfaces that interface with the outer surface of the cylindrical bag 200 may be concavely-curved as illustrated in FIGS. 11A, 11B, 12, 13A, 13B, and 14: housing surface 327; member surface 306; and/or lid (strap) 329. For example, FIG. 12 illustrates that housing surface 327 (among other surfaces including 306 and 329) defines a concave curvature $R_L$ in the longitudinal direction of cylindrical bag 200 when cylindrical bag 200 is installed in the housing as shown in FIG. 11B. This longitudinal concave curvature of surface 327 is likewise visible in other views such as FIG. 14. Next, FIG. 13A, among others, illustrates that housing surface 327 (among other surfaces including 306 and 329) defines another concave curvature $R_R$ in the radial direction of cylindrical bag 200 when cylindrical bag 200 is installed in the housing as shown in FIG. 11B. In this manner the concavely curved surfaces of the member 306 and/or surface 327 and/or lid 329 at least roughly correspond to the convexly curved outer surface of the cylindrical bag 200. The foregoing two paragraphs are meant only to describe in words what is inherently shown by the geometries depicted in the Figures.

As before, preferably there are two openings 328 and 334 for the two ends of the flexible self-inflating resuscitator squeeze bag assembly to extend through (see FIG. 11B).

Another optional feature may be to have some or most or all of the edges 312, 312a of the housing comprise soft, elastomeric edges, to absorb shocks and dings.

Another optional feature is to have substantially all of the component parts of the device 100 or 300 be non-ferromagnetic such that the device is suitable for use in an MRI suite, namely such that the magnetism does not turn the device into a missile. Preferably, this would comprise omitting motors or batteries with ferromagnetic materials. For example, the actuator may comprise a pneumatic motor (rotary, piston, or otherwise) couplable (via fitting) to a compressed air/gas outlet in such suite.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. It is also contemplated that structures and features embodied in the present examples can be altered, rearranged, substituted, deleted, duplicated, combined, or added to each other.

What is claimed is:

1. A device for use with a flexible self-inflating resuscitator squeeze bag having a generally cylindrical convexly curved outer surface when inflated, the device comprising:
   a housing having an outer surface;
   the outer surface of the housing defining at least one holding region concavely shaped to correspond to at least a portion of the generally cylindrical convexly curved outer surface of said squeeze bag;
   a mechanical compression squeezer for cyclically squeezing said squeeze bag from its outside and releasing said squeeze bag for expansion;
   a powered actuator for powering said mechanical compression squeezer for said cyclical squeezing; and,
   wherein said one holding region is adapted to hold said squeeze bag during said squeezing.

2. The device of claim 1, further comprising a confinement member adapted to confine said squeeze bag to said one holding region.

3. The device of claim 2 wherein said confinement member comprises a flexible strap.

4. The device of claim 3, wherein said confinement member is located generally opposite of said compression squeezer and wherein said mechanical compression squeezer also has a region concavely shaped to correspond to at least a portion of the generally cylindrical convexly curved outer surface of said squeeze bag.

5. The device of claim 3, wherein said powered actuator comprises an electric motor, said electric motor being within the housing, and a power base located beneath and detachable from said housing.

6. The device of claim 5, and further comprising: electronic signal means for giving a series of signals corresponding to cyclical movement of said squeeze bag.

7. The device of claim 6, wherein said confinement member leaves a portion of said squeeze bag exposed and uncovered when said confinement member confines said squeeze bag to said one holding region.

8. The device of claim 7, and further comprising:
   A pressure sensor for detecting pressure in said squeeze bag exceeding a safety threshold; and,
   An alarm set to be activated when said safety threshold is exceeded.

9. The device of claim 7, further comprising:
   said exposed and uncovered portion of said squeeze bag including areas adapted for:
   an intake tube of said squeeze bag to connect with said squeeze bag while said squeeze bag is confined to said one holding region; and
   an outlet tube of said squeeze bag to connect with said squeeze bag while said squeeze bag is confined to said one holding region.

10. The device of claim 9, and further comprising:
    an adjustable cycle controller providing operator adjustment of cycle frequency of said mechanical compression squeezer.

11. The device of claim 10, and wherein said mechanical compression squeezer comprises a rotation member and a crank member connected to the rotation member to translate rotary motion to cyclical compression squeezing.

12. The device of claim 11, wherein said crank member has a travel slot therein providing for movement pausing of said mechanical compression squeezer.

13. The device of claim 12, wherein the device is substantially all non-ferromagnetic to be suitable for use in a magnetic resonance imaging suite.

14. The device of claim 1, wherein said powered actuator is pneumatically powered.

15. The device of claim 14, wherein the device is substantially all non-ferromagnetic to be suitable for use in a magnetic resonance imaging suite.

16. The device of claim 1, wherein said mechanical compression squeezer also has a region concavely shaped to correspond to at least a portion of the generally cylindrical convexly curved outer surface of said squeeze bag.

17. The device of claim 1, wherein said powered actuator comprises an electric motor, said electric motor being within the housing, and a power base located beneath and detachable from said housing.

18. The device of claim 1, and further comprising:
    electronic signal means for giving a series of signals corresponding to cyclical movement of said squeeze bag.

19. The device of claim 2, wherein the confinement member comprises an open-close lid attached with the housing.

20. The device of claim 1, and further comprising:
    A pressure sensor for detecting pressure in said squeeze bag exceeding a safety threshold; and,
    An alarm set to be activated when said safety threshold is exceeded.

21. The device of claim 1, and further comprising:
the housing defining a first opening adapted for an intake tube of said squeeze bag to connect with said squeeze bag while said squeeze bag is confined with said housing;
a second opening in said housing adapted for an outlet tube of said squeeze bag to connect with said squeeze bag while said squeeze bag is confined with said housing; and,
a third opening in said housing, wherein said third opening allows drop-in insertion of said squeeze bag in said housing.

22. The device of claim 21, and further comprising:
an adjustable cycle controller providing operator adjustment of cycle frequency of said mechanical compression squeezer.

23. The device of claim 21, and wherein said mechanical compression squeezer comprises a rotation member and a crank member connected to the rotation member to translate rotary motion to cyclical compression squeezing, wherein said crank member has a travel slot therein providing for movement pausing of said mechanical compression squeezer.

24. The device of claim 21, and further comprising:
a flexible strap adapted to confine said squeeze bag to said one holding region.

25. A device for use with a flexible self-inflating resuscitator squeeze bag having a generally cylindrical convexly curved outer surface when inflated, the device comprising:
a portable housing having an outer surface;
the outer surface of the housing defining at least one holding region concavely shaped to correspond to at least a portion of the generally cylindrical convexly curved outer surface of said squeeze bag;
a mechanical compression squeezer in said housing for cyclically squeezing said squeeze bag from its outside and releasing said squeeze bag for expansion;
a powered actuator in said housing, including a battery and an electric motor in said housing for powering said mechanical compression squeezer for said cyclical squeezing; and
a power base located beneath and detachable from said housing, the power base adapted to provide power to the powered actuator and to charge the battery when the housing is attached to the power base.

26. The device of claim 25, and further comprising:
electronic signal means for giving a series of signals corresponding to cyclical movement of said squeeze bag.

27. The device of claim 26, and further comprising:
an adjustable cycle controller providing operator adjustment of cycle frequency of said mechanical compression squeezer.

28. The device of claim 25, and further comprising:
an adjustable cycle controller providing operator adjustment of cycle frequency of said mechanical compression squeezer.

29. A device for use with a flexible self-inflating resuscitator squeeze bag having a generally cylindrical convexly curved outer surface when inflated, the device comprising:
a housing having an outer surface;
the outer surface of the housing defining at least one holding region concavely shaped to correspond to at least a portion of the generally cylindrical convexly curved outer surface of said squeeze bag;
a mechanical compression squeezer in said housing for cyclically squeezing said squeeze bag from its outside and releasing said squeeze bag for expansion;
a powered actuator for powering said mechanical compression squeezer for said cyclical squeezing;
wherein said mechanical compression squeezer comprises a rotation member and a crank member connected to the rotation member to translate rotary motion to cyclical compression squeezing, wherein said crank member has a travel slot therein providing for movement pausing of said mechanical compression squeezer.

30. The device of claim 29, and further comprising:
a flexible strap connected with the housing and adapted to hold said squeeze bag during said cyclical squeezing.

31. The device of claim 30, and further comprising:
an adjustable cycle controller providing operator adjustment of cycle frequency of said mechanical compression squeezer.

32. A device for use with a flexible self-inflating resuscitator squeeze bag having a generally cylindrical convexly curved outer surface when inflated, the device comprising:
a housing having an outer surface;
the outer surface of the housing defining at least one holding region concavely shaped to correspond to at least a portion of the generally cylindrical convexly curved outer surface of said squeeze bag;
a mechanical compression squeezer in said housing for cyclically squeezing said squeeze bag from its outside and releasing said squeeze bag for expansion;
a powered actuator in said housing for powering said mechanical compression squeezer for said cyclical squeezing; and,
wherein the housing and its contents are substantially all non-ferromagnetic to be suitable for use in a magnetic resonance imaging suite.

* * * * *